United States Patent
Toczko et al.

(10) Patent No.: US 11,571,421 B2
(45) Date of Patent: Feb. 7, 2023

(54) GABAA POSITIVE ALLOSTERIC MODULATOR COMPOUNDS FOR TREATMENT OF ITCH AND/OR DERMATITIS

(71) Applicant: NeuroCycle Therapeutics, Inc., Cambridge, MA (US)

(72) Inventors: Matthew Toczko, Raleigh, NC (US); Jed Hubbs, Cambridge, MA (US)

(73) Assignee: NeuroCycle Therapeutics, Inc., San Diego, CA (US)

( * ) Notice: Subject to any disclaimer, the term of this patent is extended or adjusted under 35 U.S.C. 154(b) by 0 days.

(21) Appl. No.: 16/950,482

(22) Filed: Nov. 17, 2020

(65) Prior Publication Data

US 2021/0137924 A1 May 13, 2021

Related U.S. Application Data

(63) Continuation of application No. PCT/US2019/033598, filed on May 22, 2019.

(60) Provisional application No. 62/674,726, filed on May 22, 2018.

(51) Int. Cl.

| | | |
|---|---|---|
| A61K 31/5025 | (2006.01) | |
| A61P 17/04 | (2006.01) | |
| A61K 9/00 | (2006.01) | |
| A61K 31/437 | (2006.01) | |
| A61K 31/502 | (2006.01) | |

(52) U.S. Cl.
CPC ........ *A61K 31/5025* (2013.01); *A61K 9/0053* (2013.01); *A61K 31/437* (2013.01); *A61K 31/502* (2013.01); *A61P 17/04* (2018.01)

(58) Field of Classification Search
CPC ............... A61K 31/437; A61K 31/502; A61K 31/5025; A61K 47/26; A61K 47/40; A61K 9/0053; A61K 9/0095; A61K 9/08; A61K 9/1075; A61K 9/2018; A61K 9/4858; A61P 17/04
See application file for complete search history.

(56) References Cited

U.S. PATENT DOCUMENTS

| | | |
|---|---|---|
| 6,255,305 B1 | 7/2001 | Broughton et al. |
| 6,572,848 B1 | 6/2003 | Breton et al. |
| 2013/0331394 A1 | 12/2013 | Siekmeier |
| 2018/0104244 A1 | 4/2018 | Erickson et al. |

FOREIGN PATENT DOCUMENTS

| | | |
|---|---|---|
| WO | 2005030773 A1 | 4/2005 |
| WO | 2006061428 A2 | 6/2006 |
| WO | 2017/129801 | 8/2017 |

OTHER PUBLICATIONS

Gurrell et al. (British Journal of Pharmacology May 2018, vol. 175, pp. 708-725) (Year: 2018).*
Search Report for European App. No. 19808207.5 dated Oct. 1, 2021.

(Continued)

*Primary Examiner* — Savitha M Rao
(74) *Attorney, Agent, or Firm* — K&L Gates LLP

(57) ABSTRACT

Disclosed herein are GABAA positive allosteric modulators for the treatment of pruritic conditions and dermatitis. Also disclosed herein are formulations comprising the GABAA positive allosteric modulators.

26 Claims, 2 Drawing Sheets

(56) References Cited

OTHER PUBLICATIONS

Jucaite Aurelija et al; "GABAAreceptor occupancy by subtype selection GABAA[alpha]2, 3modulators: PET studies in humans," Psychopharmacology, Springer Verlog, Belin, DE, vol. 234, No. 4, Dec. 24, 2016; pp. 707-716, XP036143669; ISSN: 0033-3158, DOI: 10.1007/S00213-016-4506-4; retrieved Dec. 24, 2016.
Chinese Office Action from corresponding Chinese Patent Application No. 201780008490.1 dated Jan. 29, 2021.
Japanese Office Action from corresponding Japanese Patent Application No. 2008-539149 dated Jan. 19, 2021.
Chen et al., "GABAA Receptors in the Central Nucleus of the Amygdala are involved in Pain- and Itch-Related Responses", The Journal of Pain (2016), 17(2), pp. 181-189. (Abstract Only).
Garcia de Lucas et al., "GABAA α5 Subunit-Containing Receptors Do Not Contribute to Reversal of Inflammatory-Induced Spinal Sensitization as Indicated by the Unique Selectivity Profile of the GABAA Receptor Allosteric Modulator NS16085", Biochemical Pharmacology (2015), 93(3), pp. 370-379. (Abstract Only).
Kohut et al., "Novel Discriminative Stimulus Effects of TPA023B, Subtype-Selective γ-aminobutyric-acidA Benzodiazepine Modulator: Comparisons with Zolpidem, Lorazepam, and TPA023," Pharmacology Biochemistry and Behavior (2008), 90(1), pp. 65-73.

\* cited by examiner

GABAA POSITIVE ALLOSTERIC MODULATOR COMPOUNDS FOR TREATMENT OF ITCH AND/OR DERMATITIS

CROSS-REFERENCE

This application is a continuation of International Application No. PCT/US2019/033598, filed May 22, 2019 which claims the benefit of U.S. Provisional Application No. 62/674,726, filed May 22, 2018, each of which is entirely incorporated herein by reference for all purposes.

BACKGROUND

Itch is an unpleasant sensation of the skin that elicits the desire to scratch. Common causes of inch include, for example, xerosis, skin conditions and insect bites. Most cases of itching are treated with H1-antihistamines, which work reliably if the cause of itching is histamine related. However, many cases of itch are not histamine related. Thus, there remains a need for pharmaceutical compounds that are suitable for treating itch.

SUMMARY

Disclosed herein are methods of treating or preventing itch in a mammal in need thereof, comprising administering to said mammal a pharmaceutical composition that comprises a therapeutically effective amount of a GABBA modulating compound of formula I, II, or A,

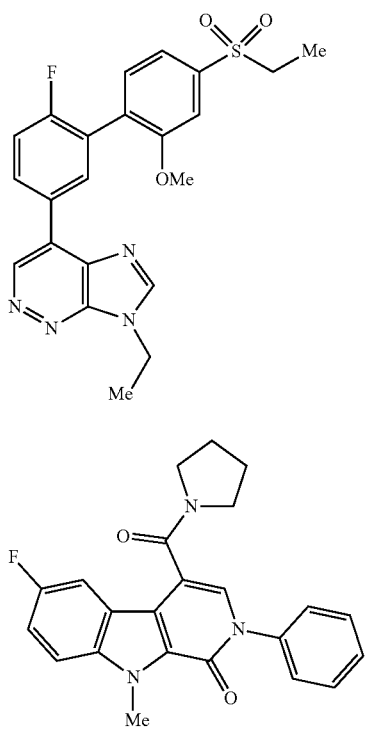

I

II

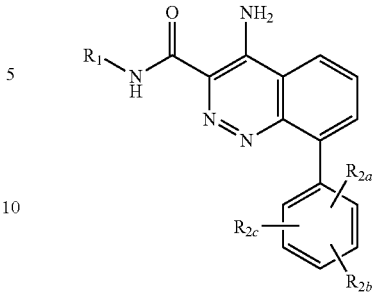

A a derivative thereof, or a pharmaceutically acceptable prodrug, salt, solvate, hydrate, or co-crystal thereof, where: $R_1$ is hydrogen, alkyl, substituted alkyl, aryl, substituted aryl, benzyl, substituted benzyl, $C(=O)A_1$, or $C(=O)OA_2$; or $R_{2a}$, $R_{2b}$, and $R_{2c}$ are independently hydrogen, halogen, $C_{1-8}$ alkyl, $C_{1-8}$ haloalkyl, heteroalkyl, $C_{3-8}$ cycloalkyl, amino, cyano, nitro, aryl, heteroaryl, aminoacyl, acylamino, OH, or OR'; where $A_1$ and $A_2$ are independently hydrogen, alkyl or substituted alkyl; or R' can be independently methyl, ethyl, n-propyl, i-propyl, n-butyl, i-butyl, s-butyl, t-butyl, cyclopropyl, cyclobutyl, cyclopentyl, cyclohexyl, cyclopropylmethyl or phenyl. In some embodiments, said pharmaceutical composition is administered orally. In some embodiments, said pharmaceutical composition is administered through rectal administration. In some embodiments, said pharmaceutical composition is administered parenterally. In some embodiments, the itch is associated with a disease or disorder selected from LIST 1. In some embodiments, the itch is associated with atopic dermatitis, uremic pruritus, or neuropathic itch. In some embodiments, the compound is of Formula A. In some embodiments, $R_1$ is $C_1$-$C_6$ alkyl, $R_{2a}$ is hydrogen, $R_{2b}$ is halogen, and $R_{2c}$ is OMe. In some embodiments, $R_1$ is $C_1$-$C_6$ alkyl, $R_{2a}$ is hydrogen, and $R_{2b}$ and $R_{2c}$ are OMe. In some embodiments, said compound is PF-06372865. In some embodiments, said compound has a structure of Formula I,

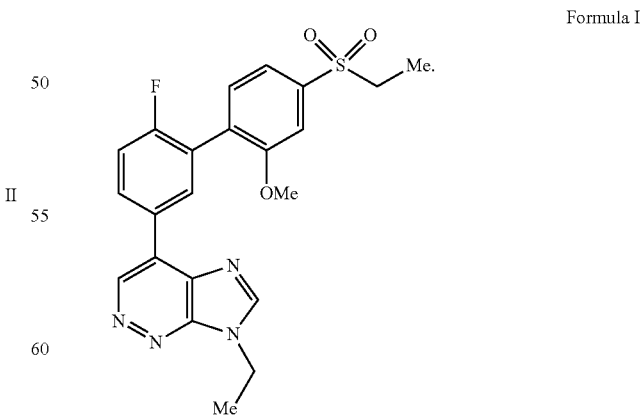

Formula I

In some embodiments, said compound is SL65.1498. In some embodiments, said compound has a structure of Formula II, pharmaceutically acceptable prodrug, salt, solvate, hydrate, or co-crystal thereof. In some embodiments, said pharmaceutical composition is administered orally. In some embodiments, said pharmaceutical composition is administered through rectal administration. In some embodiments, said pharmaceutical composition is administered parenterally. In some embodiments, said dermatitis is selected from eczema, atopic dermatitis, seborrheic dermatitis, contact dermatitis, irritant dermatitis, summer recurrent dermatitis, and dermatitis herpetiformis. In some embodiments, In some embodiments, said compound is PF-06372865. In some embodiments, said compound has a structure of Formula I, Formula I

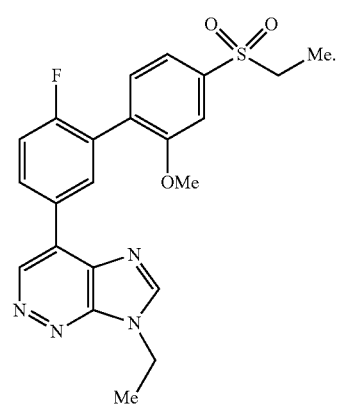

In some embodiments, said compound is SL65.1498. In some embodiments, said compound has a structure of Formula II, Formula II

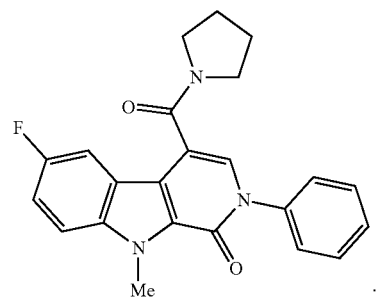

In some embodiments, said compound is AZD7325. In some embodiments, said compound has a structure of Formula III, Formula III

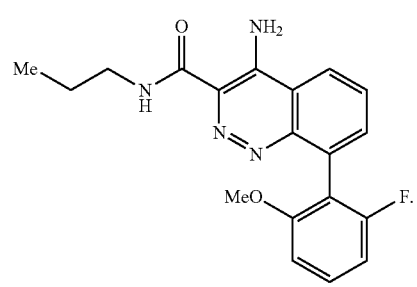

In some embodiments, said compound is AZD6280. In some embodiments, said compound has a structure of Formula IV, Formula IV

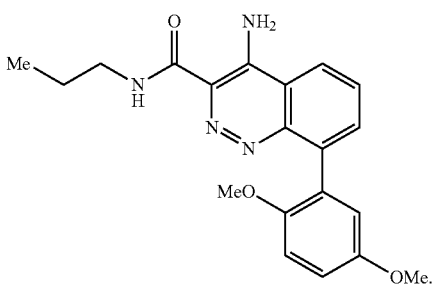

In some embodiments, said pharmaceutical composition comprises an emulsifying agent, a percutaneous penetration enhancer, a suspending agent, water, or any combination thereof. In some embodiments, said emulsifying agent comprises an ethoxylated fatty acid. In some embodiments, said percutaneous penetration enhancer comprises glycerol. In some embodiments, said suspending agent comprises hydroxypropyl-beta-cyclodextrin. In some embodiments, the therapeutically effective amount comprises from about 0.01 mg to about 200 mg of the GABAA modulating compound. In some embodiments, the therapeutically effective amount comprises from about 0.05 mg to about 100 mg of the GABAA modulating compound.

Also disclosed herein are methods of treating or preventing dermatitis in a mammal in need thereof, comprising administering to said mammal a pharmaceutical composition that comprises a therapeutically effective amount of a GABBA modulating compound selected from PF-06372865, SL65.1498, AZD7325, and AZD6280, or a Formula II

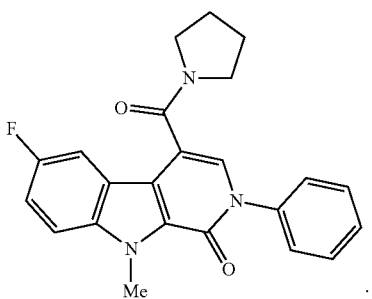

In some embodiments, said compound is AZD7325. In some embodiments, said compound has a structure of Formula III, Formula III

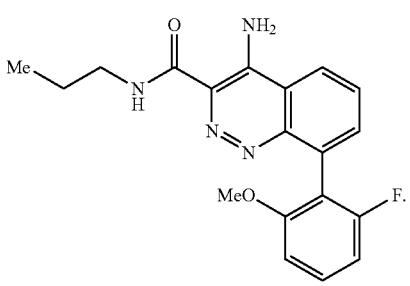

In some embodiments, said compound is AZD6280. In some embodiments, said compound has a structure of Formula IV, Formula IV

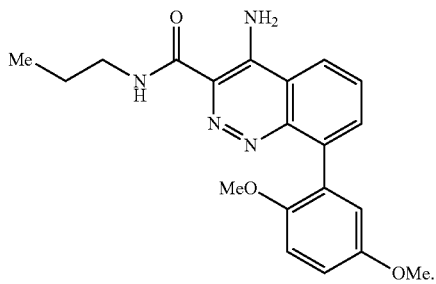

In some embodiments, said pharmaceutical composition comprises an emulsifying agent, a percutaneous penetration enhancer, a suspending agent, water, or any combination thereof. In some embodiments, said emulsifying agent comprises an ethoxylated fatty acid. In some embodiments, said percutaneous penetration enhancer comprises glycerol. In some embodiments, said suspending agent comprises hydroxypropyl-beta-cyclodextrin. In some embodiments, the therapeutically effective amount comprises from about 0.01 mg to about 200 mg of the GABAA modulating compound. In some embodiments, the therapeutically effective amount comprises from about 0.05 mg to about 100 mg of the GABAA modulating compound.

Also disclosed herein are medicaments for use in the treatment or prevention of itch or dermatitis, said medicament comprises a therapeutically effective amount of a compound of Formula I, II, III, or IV:

I

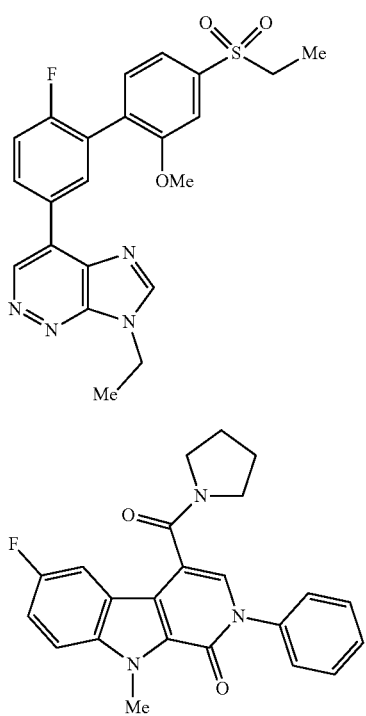

II

-continued

III

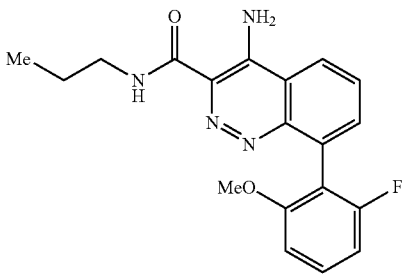

IV

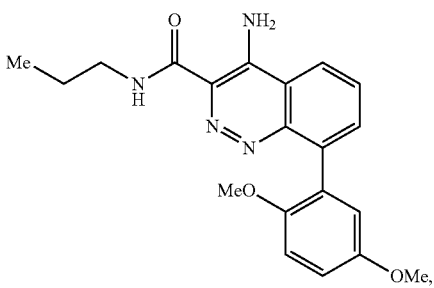

a derivative thereof, or pharmaceutically acceptable prodrug, salt, solvate, hydrate, or co-crystal thereof.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

BRIEF DESCRIPTION OF THE DRAWINGS

The novel features of exemplary embodiments are set forth with particularity in the appended claims. A better understanding of the features and advantages will be obtained by reference to the following detailed description that sets forth illustrative embodiments, in which the principles of exemplary embodiments are utilized, and the accompanying drawings of which:

FIG. 1A depicts the total number of scratch bouts observed over a 30 minute time period post CQ injection. FIG. 1B depicts the average number of scratching bouts observed in 5 minute intervals for the 30 minute time period.

FIG. 2A depicts the total number of scratch bouts observed over a 30 minute time period post CQ injection. FIG. 2B depicts the average number of scratching bouts observed in 5 minute intervals for the 30 minute time period.

DETAILED DESCRIPTION

I. Overview

Figure 1A:
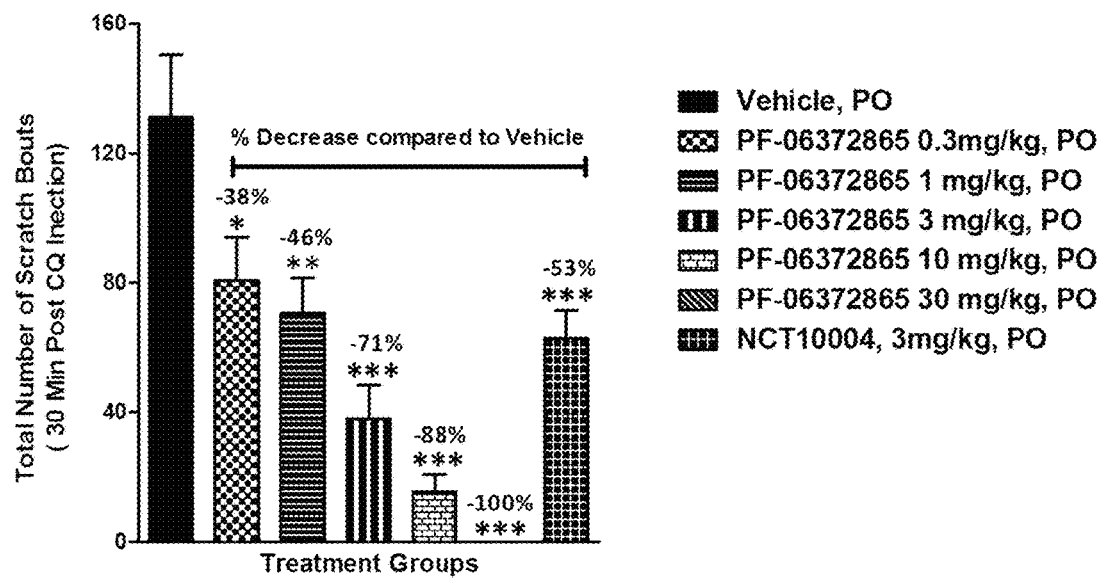
FIGS. 1A-1B depict the effect of PF-06372865 on a Chloroquine (CQ)-Induced Itch Model in Male C57BL/6 Mice. Data is represented as Mean±SEM, (n=9 animals/group/time point).

Disclosed herein are compounds of formulae I, II, III, or IV including any pharmaceutically acceptable prodrug, salt, solvate, hydrate, or co-crystal thereof, or derivative thereof, for use in the treatment or prevention of itch and/or dermatitis. In some embodiments, disclosed herein are methods of prevention or treatment of itch and/or dermatitis with compositions containing compounds of formulae I, II, III, or IV including any pharmaceutically acceptable prodrug, salt, solvate, hydrate, or co-crystal thereof. Compositions for pharmaceutical or veterinary use comprising one or more compounds are also described herein.

The compounds of formula I, II, and A have the following structures:

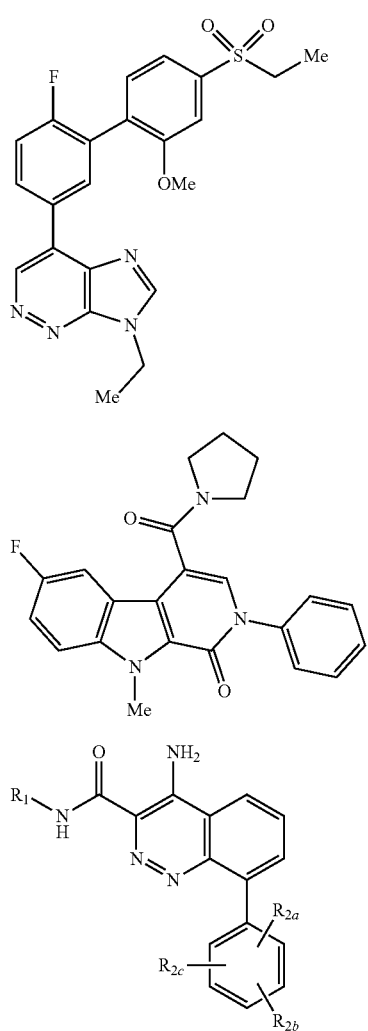

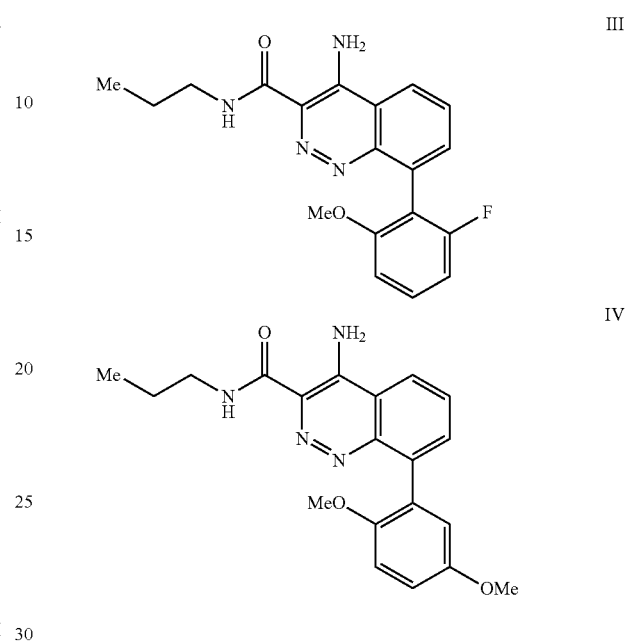

where: $R_1$ is hydrogen, alkyl, substituted alkyl, aryl, substituted aryl, benzyl, substituted benzyl, C(=O)A$_1$, or C(=O)OA$_2$; or $R_{2a}$, $R_{2b}$, and $R_{2c}$ are independently hydrogen, halogen, $C_{1-8}$ alkyl, $C_{1-8}$ haloalkyl, heteroalkyl, $C_{3-8}$ cycloalkyl, amino, cyano, nitro, aryl, heteroaryl, aminoacyl, acylamino, OH, or OR'; where $A_1$ and $A_2$ are independently hydrogen, alkyl or substituted alkyl; or R' can be independently methyl, ethyl, n-propyl, i-propyl, n-butyl, i-butyl, s-butyl, t-butyl, cyclopropyl, cyclobutyl, cyclopentyl, cyclohexyl, cyclopropylmethyl or phenyl. In some embodiments, a compound can be a compound of Formula A, where $R_1$ is $C_1$-$C_6$ alkyl, $R_{2a}$ is hydrogen, $R_{2b}$ is halogen, and $R_{2c}$ is OMe. In some embodiments, a compound can be a compound of Formula A, where $R_1$ is $C_1$-$C_6$ alkyl, $R_{2a}$ is hydrogen, and $R_{2b}$ and $R_{2c}$ are OMe. In some cases, a compound of Formula A can be a compound of Formula III or Formula IV:

II. Definitions

As used herein, the term "itch", also known as pruritus, refers to the sensation that elicits a reflex response to scratch. Itch can be a symptom of a disease, disorder or infection, or itch can arise spontaneously, without an underlying or identifiable physiological cause, known as idiopathic pruritus.

As used herein, the term "treatment" refers to all aspects of control of itching including therapy. Control of itch includes reducing, alleviating, relieving and numbing the sensation of itch. Control of itch also includes reducing the desire to scratch.

As used herein, the term "prevent" or "prevention" refers to stopping, hindering, and/or slowing down the onset of itch sensations and symptoms, wherein the itch sensations and symptom can be associated with medical conditions or have no known etiology.

As used herein, the term "therapeutically effective amount" and grammatical variations thereof refer to quantities of the active compound that can produce the desired therapeutic effect when administered to a mammal afflicted with pruritus and/or dermatitis. The term "therapeutic effect" is used herein in a broad sense and includes prophylactic effects. Desired therapeutic effects include but are not limited to reduced sensation of itch, reduced distraction due to the itch sensation, the reduced desire to scratch, and/or reduced skin lesions (erythema, induration/papulation, and/or marked lichenification).

As used herein, the term "comprising" and grammatical variations thereof means that other elements can also be present in addition to the defined elements presented. The use of "comprising" indicates inclusion rather than limitation.

As used herein, the term "dermatitis" means an inflammatory skin disease with characteristics that include one or more of the following: erythema, induration/papulation, and/or marked lichenification.

As used herein, the term "lesion" means any abnormal change involving any tissue due to disease or injury, but with a special emphasis on the skin, including dermatitis, nodules, blisters, urticaria, erythema, papulation, lichenification, etc.

As used herein, the term "compound" includes any pharmaceutically acceptable salt, solvate, prodrug, hydrate, or co-crystal thereof.

As used herein, the term "prodrug" can refer to a compound that may not fully satisfy the structural requirements of the compounds provided herein, but is modified in vivo, following administration to a patient, to produce a compound described herein, or other formula provided herein. For example, a prodrug may be an acylated derivative of a compound as provided herein. Prodrugs include compounds wherein hydroxy, amine or sulfhydryl groups are bonded to any group that, when administered to a mammalian subject, cleaves to form a free hydroxy, amino, or sulfhydryl group, respectively. Examples of prodrugs include, but are not limited to, acetate, formate and benzoate derivatives of alcohol and amine functional groups within the compounds provided herein. Prodrugs of the compounds provided herein may be prepared by modifying functional groups present in the compounds in such a way that the modifications are cleaved to the parent compounds.

As used herein, the term "derivative" of a parent compound can include any substitution, either direct or indirect, to a compound provided herein that retains the positive allosteric modulatory ability of the parent compound. Such "derivatives" can include a prodrug, a metabolite, an enantiomer, a diastereomer, a labeled compound (i.e. an compound labeled with an isotope such as $^2H$, $^3H$, $^{13}C$, $^{14}C$, $^{15}N$, $^{18}O$, $^{17}O$, $^{31}P$, $^{32}P$, $^{35}S$, $^{18}F$, or $^{36}Cl$), esters (e.g. acyloxyalkylesters, alkoxycarbonyloxyalkyl esters, alkyl esters, aryl esters, phosphate esters, sulfonate esters, sulfate esters and disulfide containing esters), ethers, amides, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts, sulfonate esters, and the like. In some cases, a derivative may include trivial substitutions (i.e. additional alkyl/akylene groups) to a parent compound that retains the positive allosteric modulatory ability of the parent compound.

III. Treatment of Itch

Disclosed herein are new treatments for all types of itch. In some embodiments, disclosed herein are new treatments for all types of dermatitis with particular emphasis on atopic dermatitis and contact dermatitis. Also disclosed herein is the use of Gamma-aminobutyric acid (GABA) receptor modulator compounds for treatment of atopic dermatitis and contact dermatitis.

GABA receptor modulators as described herein and pharmaceutical or veterinary compositions (medicaments) containing them have potential in the treatment of all types of itch and/or the treatment of dermatitis.

Itch (lat. pruritus) is an unpleasant sensation of the skin that elicits the desire to scratch. The intensity of itching can be mild, moderate or severe resulting in sleep disorders, discomfort and increased irritability or general stress. Symptoms of generalized itch may be related to a variety of different reasons. Itching can be provoked or enhanced by a number of chemical substances such as histamine, prostaglandins, proteases, cytokines, neuropeptides, in particular substance P, and bile salts. Some of the substances act directly on the free nerve ending, while others act indirectly through mast cells or other cells. Factors that are believed to enhance the sensation of itching include dryness of the epidermis and dermis, anoxia of tissues, dilation of the capillaries, irritating stimuli, primary skin diseases and psychiatric disorders.

The itching sensation is transmitted from peripheral nerves via the dorsal horn of the spinal cord to the brain. However, inhibitory receptors present in nerve fibers involved in the transmission of the itching signal to the brain are not well studied, although they might represent a promising drug target to alleviate the itching sensation independent of the cause. Most cases of itching are treated with H1-antihistamines, which work reliably if the cause of itching is histamine related. Common causes of itch are further described below. Other medications used against itching comprise corticosteroids, gabapentinoides, opioid-receptor antagonists, capsaicin and local anaesthetics. Most of these medications can have unwanted side-effects, especially when used systemically. Itch is a common problem and can be localized (limited to one area of the body) or generalized (occurring all over the body or in several different areas). The medical term for itching is pruritus. Generalized itch, for obvious reasons, is more difficult to treat than localized itch. Itch can also occur with or without skin lesions (for example, papules, nodules or blisters).

Itch can originate in the peripheral nervous system (dermal or neuropathic) or in the central nervous system (neuropathic, neurogenic, or psychogenic). Itch originating in the skin is considered pruritoceptive and can be induced by a variety of stimuli, including mechanical, chemical, thermal, and electrical stimulation. The primary afferent neurons responsible for histamine induced itch are unmyelinated C-fibers. In human C-fiber nociceptors, two major classes exist: mechano-responsive nociceptors and mechano-insensitive nociceptors. Mechano-responsive nociceptors have been shown in studies to respond to mostly pain and mechano-insensitive receptors respond mostly to itch induced by histamine. The feeling of itchiness can be caused by a movement of hair or the release of a chemical (histamine) from cells under the skin. Itchiness is regarded as protective when it helps creatures remove parasites that land on their skin.

Itching usually prompts scratching, which can lead to a vicious itch-scratch cycle. Scratching can initially feel satisfying, but prolonged scratching leaves one with irritated skin that can itch worse than it did prior to scratching, which leads to more scratching. Furthermore, scratching may cause itching in and of itself. Since scratching provides only temporary relief and does not promote healing of the underlying problem, it is best to avoid scratching if at all possible. If scratching breaks open the skin, bacterial infection can set in. And if scratching continues for many months or years, the area that is scratched may develop thickened skin (lichenification) or pigmentation that darkens the area. Obviously, the best way to allow irritated skin to heal is to stop scratching it. However, will power often is not enough since the urge to scratch can be compelling in both human and animal patients. Thus, disclosed herein are alternative means for treatment of all types of itch and/or pruritic skin lesions in humans and non-human animals by administering to a human or non-human subject in need thereof a GABA receptor modulator compound in an amount sufficient to at least partially ameliorate the itch and/or pruritic skin lesion.

In some embodiments, a compound as described herein can be used to treat neuropathic itch. Neuropathic itch can originate at any point along the afferent pathway as a result of damage of the nervous system. They could include diseases or disorders in the central nervous system or peripheral nervous system. Examples of neuropathic itch in origin are nostalgia paresthetica, brachioradial pruritus, brain tumors, multiple sclerosis, peripheral neuropathy, and nerve irritation.

In some embodiments, a compound as described herein can be used to treat neurogenic itch. Neurogenic itch, which is itch induced centrally but with no neural damage, is often associated with increased accumulation of endogenous opioids and possibly synthetic opioids.

In some embodiments, a compound described herein can be used to treat itch associated with a psychiatric disorder. Itch is also associated with some psychiatric disorders such as delusions of parasitosis or related obsessive-compulsive disorders, for example neurotic scratching or skin picking.

In some embodiments, a compound described herein can be used to treat itch associated with other conditions. For example, xerosis, is a common cause, frequently seen in winters. It is associated with older age, frequent bathing in hot showers or baths, and high temperature and low humidity environments. Skin conditions (such as psoriasis, eczema, sunburn, athlete's foot, hidradenitis suppurativa and many others) are also other common causes. Most are of an inflammatory nature. Other causes include but are not limited to: insect bites, such as those from mosquitoes, fleas or chiggers; allergic reactions to contact with specific chemicals, such as urushiol from poison ivy or poison oak; cancers of the blood such as Hodgkin's disease; jaundice where the built up of bilirubin is a skin irritant at high concentrations; polycythemia, which can cause generalized itching due to increased histamine; scabies or infection with lice or worms; liver, kidney, and thyroid illnesses; shaving, which can irritate the skin; diabetes mellitus; dandruff where there is an unusually large amount of epidermal flaking associated with this sensation; iron deficiency such as anemia; parasitic infections such as certain parasites of birds and mammals that are released from infected snails in fresh and saltwater and they cause swimmer's itch, also called cercarial dermatitis; allergy to psychiatric medication; fungal infections, e.g. of the crotch (tinea cruris) commonly known as jock itch, as well as vaginal itching and/or anal itching from sexually transmitted diseases (STDs) or other types of infections; photodermatitis—sunlight reacts with chemicals in the skin, leading to the formation of irritant metabolites, for example, sunburn; directly contact or ingestion of chemical compounds or drugs, e.g. morphine and other opiates; cholestasis related to pregnancy: pruritic urticarial papules and plaques of pregnancy (PUPPP); and gestational pemphigoid. Causes of itch can also be psychological, that is, due to stress, anxiety, etc., and stress also can aggravate itch from other causes.

In some embodiments, a compound described herein can be used to treat itch caused by or associated with a condition recited in List 1.

List 1:
(a.) Skin conditions, comprising dermatitis herpeformis, psoriasis, eczema, seborrheic dermatitis, atopic eczematous dermatitis, atopic dermatitis, summer recurrent dermatitis, contact dermatitis, irritant dermatitis, xerosis (dry skin), urticaria, hidradenitis suppurativa, lichen planus, lichen simplex, lichen simplex chronicus, lichen sclerosis, sweat gland abnormalities, bullous pemphigoid, pruritic urticarial papules and plaques of pregnancy (PUPPP), gestational pemphigoid, etc.
(b.) Cholestasis, which may result from several disorders comprising liver cirrhosis, gallstones, primary biliary cirrhosis, pregnancy, some medications or drugs, jaundice, hepatitis, abdominal masses, cystic fibrosis, cancer; etc.
(c.) Renal disorders comprising chronic kidney disease, also known as uremic pruritus; hemodialysis, cancer, etc.
(d.) Infections including fungal infections comprising vaginal or anal yeast infection, athlete's foot, or jock itch; viral infections, comprising chicken pox, shingles, some sexually transmitted diseases; bacterial infections of the skin, including acne; and parasitic infections or infestations comprising scabies, lice or worm infections; swimmer's itch; etc.
(e.) Insect bites or stings, such as those from mosquitoes, fleas, chiggers, spiders, scorpions, biting flies, bees, wasps, hornets, mites, ants, etc.
(f.) Medications or other chemicals including allergy to psychiatric medications or antibiotics in particular; morphine and other opioid-induced itch; photodermatitis, where sunlight reacts with chemicals in the skin forming irritant molecules; and chemotherapy.
(g.) Other causes comprising cancers of the blood such as Hodgkin's disease; skin cancers; cutaneous T-cell lymphoma.; other forms of cancer; polycythemia, which can cause generalized itching due to increased histamine; thyroid illnesses; shaving; diabetes mellitus; dandruff; iron deficiency such as anemia; psychogenic itch; stress and stress disorders; sunburn; senile itch; idiopathic itch; burns; wound healing; skin blisters, prurigo nodularis chronic pruritus; and neurogenic itch, or itch related to nerve damage; multiple sclerosis; pinched nerves; etc.

In some embodiments, a compound described herein can be used to treat dermatitis. In its broadest sense, dermatitis is inflammation of the skin that occurs with itch. It is a common and disfiguring skin condition which requires quick and efficient treatment. Dermatitis symptoms vary, however, with the different forms of the condition. Symptoms vary from smooth rashes to bumpy rashes through to flaky skin and blisters. Although different types of dermatitis have varying symptoms, there are certain signs that are common for all of them, including redness of the skin, swelling, itching, skin lesions and sometimes oozing and scarring.

Also, the area of the skin on which the symptoms appear tends to be different with every type of dermatitis. Types of dermatitis are classified according to the cause of the condition. In some embodiments, a compound described herein can be used to treat contact dermatitis. Contact dermatitis is caused by an allergen or an irritating substance. Irritant contact dermatitis accounts for 80% of all cases of contact dermatitis. In some embodiments, a compound described herein can be used to treat atopic dermatitis. Atopic dermatitis is very common worldwide and increasing in prevalence. Atopic dermatitis is a type of eczema and is an inflammatory, chronically relapsing, non-contagious and itchy skin disorder.

In some embodiments, a compound described herein can be used to treat other less common forms of dermatitis, including dermatitis herpetiformis, seborrheic dermatitis, stasis dermatitis, and infective dermatitis. Dermatitis herpetiformis is characterized by intensely itchy, chronic papulovesicular eruptions, usually distributed symmetrically on extensor surfaces such as the back of neck, scalp, elbows, knees, back, hairline, groin or face. Seborrheic dermatitis is a dermatitis that occurs in the vicinity of sebaceous glands and is caused by sebum over production. The condition tends to give a scaly, flaky skin condition. Stasis dermatitis is an inflammation on the lower legs which is caused by buildup of blood and fluid and it is more likely to occur in people with varicose veins. Infective dermatitis is dermatitis secondary to a skin infection. A summary of dermatitis can be found in Blauvelt et al in Chapter 11 of J Allergy Immunol February 2003.

In some embodiments, a compound as described herein can be used to treat itch or dermatitis in conjunction with additional therapies. There are numerous therapies for dermatitis on the market. Treatment of dermatitis is made according to the particular cause of the disease. In some embodiments, a compound as described herein can be administered with a corticosteroid. Creams that contain corticosteroids are frequently used and simply avoiding the allergens and irritants are part of most treatment plans. In some embodiments, a compound as described herein can be administered with a non-steroidal medication. For some types of dermatitis, non-steroidal medications may help relieve signs and symptoms. In some embodiments, a compound as described herein can be administered with an antihistamine. For all types of dermatitis, occasional use of over-the-counter antihistamines can reduce itching. In some embodiments, a compound as described herein can be administered with other topical creams or lotions. For example, calamine lotion type products might be applied to the skin or a barrier cream such as zinc oxide or a suntan lotion might be used. In some embodiments, a compound as described herein can be administered with treatments in development or recently marketed, including IL-4/IL-13 monoclonal antibodies, topical PDE4B inhibitors, and NK1 antagonists.

IV. GABAA Modulators

GABA has been identified as a major inhibitory neurotransmitter, and agents that modulate GABAergic neurotransmission are used extensively in the treatment of conditions such as epilepsy, anxiety and depression. Two families of GABA receptor have been described, termed GABAA and GABAB. The GABAA receptor is a member of the ligand-gated ion channel superfamily. The functional receptor generally comprises a number of subunits. At least 16 such subunits have been characterized, including 6 alpha subunits (alpha1-6), 3 beta subunits (beta1-3), 3 gamma subunits (gamma1-3), and delta, epsilon, pi and theta subunits. Most GABAA receptors are made up of 2 alpha, 2 beta, and one gamma subunit. Several drug binding sites have been described. These include the binding site for the endogenous ligand (GABA), and allosteric binding sites. Drugs that bind at the allosteric binding sites may be positive allosteric modulators, which increase responsiveness, negative allosteric modulators, which decrease receptor responsiveness, or neutral, which term refers to compounds that bind to the allosteric binding sites without modulating the activity of the receptor. Recent evidence has suggested that GABAA receptors comprising either the alpha2 or alpha3 subunit (herein termed GABAA alpha2/3 receptors) may be involved in certain pain states, and that positive allosteric modulators of these receptors may be useful analgesics.

There is a continuing interest in finding new compounds that interact with GABAA receptors, and particularly for compounds that have a reduced propensity for causing the adverse events (such as drowsiness) that are associated with the currently available GABAA modulators such as benzodiazepines. These adverse effects may be the result of modulation of alpha1 subunit-containing receptors, and so preferred compounds according to the disclosure will have a high affinity for the alpha2/3 subunit-containing receptors with good efficacy as positive allosteric modulators, while having low efficacy at receptors with other alpha subunits, particularly the alpha 1 subunit-containing receptors. These drug candidates should additionally have one or more of the following properties: be well absorbed from the gastrointestinal tract; be metabolically stable; have a good metabolic profile, in particular with respect to the toxicity or allergenicity of any metabolites formed; or possess favorable pharmacokinetic properties while retaining their activity profile. They should be non-toxic and demonstrate few side-effects. Ideal drug candidates should exist in a physical form that is stable, non-hygroscopic and easily formulated.

Described herein are methods of treating or preventing itch and/or dermatitis by administering GABAA modulating compounds. In one aspect, described herein are methods of treating or preventing itch and/or dermatitis by administering one or more compounds of Formula I, II, or A:

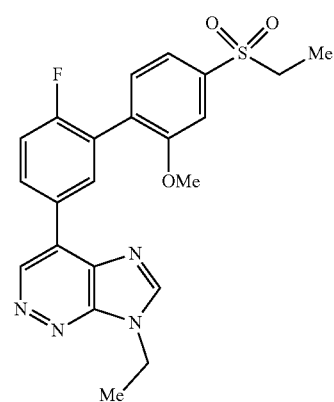

I

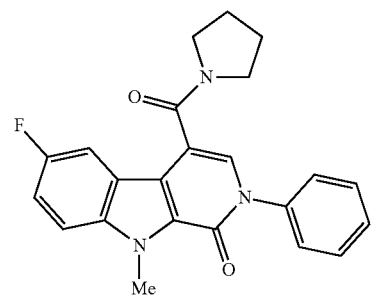

II

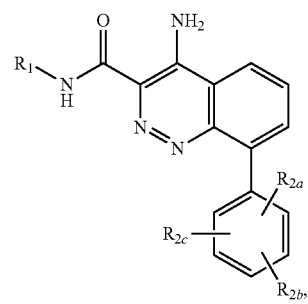

A including any pharmaceutically acceptable prodrug, salt, solvate, hydrate, or co-crystal thereof, where: $R_1$ is hydrogen, alkyl, substituted alkyl, aryl, substituted aryl, benzyl, substituted benzyl, C(=O)A$_1$, or C(=O)OA$_2$; or $R_{2a}$, $R_{2b}$, and $R_{2c}$ are independently hydrogen, halogen, $C_{1-8}$ alkyl, $C_{1-8}$ haloalkyl, heteroalkyl, $C_{3-8}$ cycloalkyl, amino, cyano, nitro, aryl, heteroaryl, aminoacyl, acylamino, OH, or OR'; where $A_1$ and $A_2$ are independently hydrogen, alkyl or substituted alkyl; or R' can be independently methyl, ethyl, n-propyl, i-propyl, n-butyl, i-butyl, s-butyl, t-butyl, cyclopropyl, cyclobutyl, cyclopentyl, cyclohexyl, cyclopropylmethyl or phenyl. In some embodiments, a compound can be a compound of Formula A, where $R_1$ is $C_1$-$C_6$ alkyl, $R_{2a}$ is hydrogen, $R_{2b}$ is halogen, and $R_2$ is OMe. In some embodiments, a compound can be a compound of Formula A, where $R_1$ is $C_1$-$C_6$ alkyl, $R_{2a}$ is hydrogen, and $R_{2b}$ and $R_{2c}$ are OMe. In some cases, a compound of Formula A can be a compound of Formula III or Formula IV:

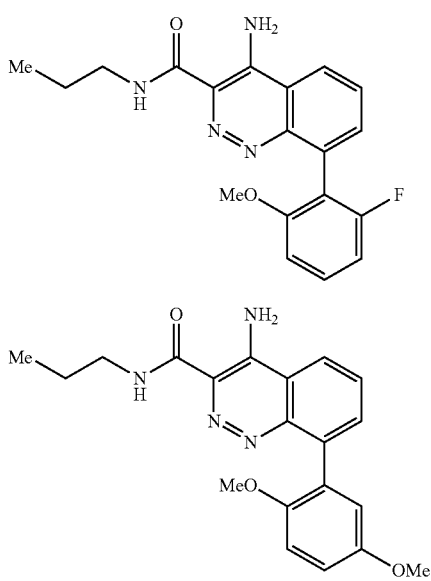

The compound(s) is administered at a therapeutically effective dosage for a therapeutically effective amount of time. One-time dosage units may be used. Alternatively, dosages may be repeated, such as hourly, twice daily, daily, weekly, monthly, etc.

In some embodiments, a compound useful for treatment itch may include a pharmaceutically acceptable salt. Typically, a pharmaceutically acceptable salt may be readily prepared by many methods known to one skilled in the art, often using a desired acid. For illustration, the salt may precipitate or crystallize from solution upon adding an acid to a solution of the unprotonated form of the desired compound, and then be collected by filtration; or by stirring a slurry of said compound in an acidic solution for a period of time, and then collecting the salt by filtration or by direct evaporation of the solvent. In some aspects, an aqueous solution of an acid may be used. For example, hydrochloric acid may be added to an aqueous suspension of a compound and the resulting mixture evaporated to dryness (lyophilized) to obtain the acid addition salt as a solid. In some aspects, a compound may be dissolved in a suitable solvent, for example an alcohol such as isopropanol, and the acid may be added in the same solvent or another suitable solvent. The resulting acid addition salt may then be precipitated directly, or by addition of a less polar solvent, and isolated by filtration.

Pharmaceutically acceptable counterions for salts are known to those skilled in the art. They may be inorganic or organic in nature. Some illustrative examples of pharmaceutically acceptable counterions comprise chloride, bromide, iodide, sulfate, bisulfate, nitrate, phosphate, hydrogen phosphate, acetate, maleate, malate, malonate, fumarate, lactate, tartrate, citrate, formate, gluconate, succinate, pyruvate, oxalate, oxaloacetate, trifluoroacetate, saccharate, benzoate, and alkyl or aryl sulfonates (for example, methanesulfonate, 1-napsylate, 2-napsylate, camsylate, ethane sulfonate, benzenesulfonate, p-toluenesulfonate, and isethionate).

In some embodiments, a compound for treating itch and/or dermatitis can be a compound of Formula I. The compound of Formula I is an alpha2/alpha3 GABAA receptor positive allosteric modulator also known as PF-06372865. (Nickolls et al. Br. J. Pharmacol. 2018, 174, 708-725).

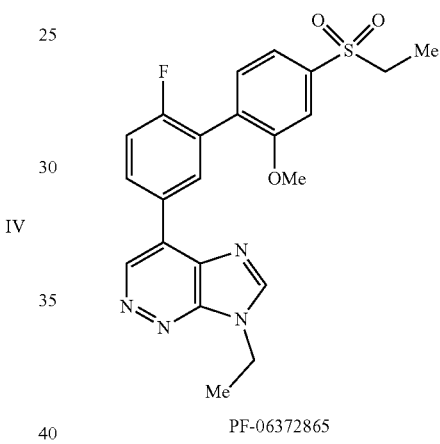

PF-06372865

In some embodiments, the compound to be used for treating itch and/or dermatitis is PF-06372865.

In some embodiments, a compound for treating a pruritic condition can be a compound of Formula II. The compound of Formula II is also known as SL65.1498 (Griebel et. al. J. Pharmacol. Exp. Ther. 2001, 298, 753-768).

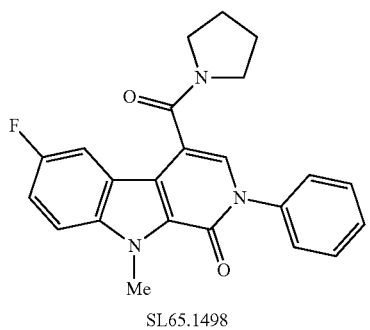 [SMILES: Cn1c2ccc(F)cc2c2c(C(=O)N3CCCC3)cn(-c3ccccc3)c(=O)c21]

SL65.1498

In some embodiments, the compound to be used for treating itch and/or dermatitis is SL65.1498.

In some embodiments, a compound for treating a pruritic condition can be a compound of Formula III. The compound of Formula III is also known as AZD7325. (Zhou et. al. Br. J. Clin. Pharmacol. 2011, 74, 98-108).

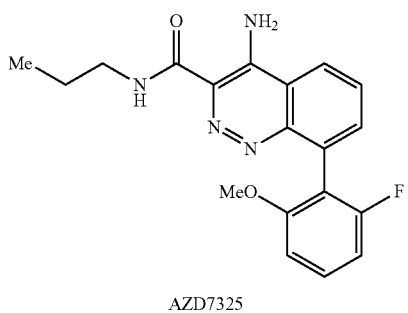 [SMILES: CCCNC(=O)c1nnc2c(-c3c(F)cccc3OC)cccc2c1N]

AZD7325

In some embodiments, the compound to be used for treating itch and/or dermatitis is AZD7325.

In some embodiments, a compound for treating a pruritic condition can be a compound of Formula IV. The compound of Formula IV is also known as AZD6280. (Artelsmair et. al. J. Label. Compd. Radiopharm. 2017, 61, 415-426; Alhambra et. al Bioorganic Med. Chem. 2011, 19, 2927-2738).

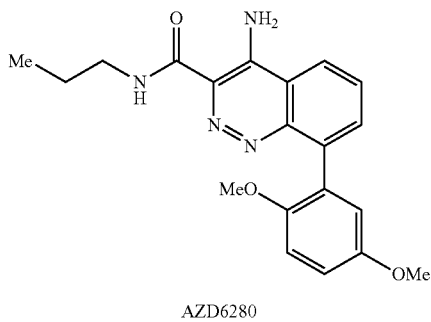 [SMILES: CCCNC(=O)c1nnc2c(-c3cc(OC)ccc3OC)cccc2c1N]

AZD6280

In some embodiments, the compound to be used for treating itch and/or dermatitis is AZD6280.

In some embodiments, a compound for treating a pruritic condition can be a combination of two or more compounds of Formula I, Formula II, or a compound of Formula A.

In some embodiments, a compound of Formula I, Formula II, or Formula A may be present in a pharmaceutically acceptable composition, also known as a formulation or dosage form wherein the compound is in a mixture with a pharmaceutically acceptable carrier or carriers selected with regard to the intended route of administration and standard pharmaceutical or veterinary practice. In some embodiments, a pharmaceutical composition can be formulated as a tablet, capsule, ampoule etc. In some embodiments, pharmaceutical or veterinary formulations (medicaments) comprising the active compound dispersed with a pharmaceutically acceptable carrier can be used to treat itch or dermatitis as described herein.

The term "carrier" refers to a diluent, excipient, and/or vehicle with which an active compound is administered. Pharmaceutical or veterinary compositions (medicaments) as described herein may contain combinations of more than one carrier. Such pharmaceutical carriers are well known in the art. The compositions may also comprise any suitable binder(s), lubricant(s), Suspending agent(s), coating agent(s), flavorant(s), stabilizer(s), dissolution agent(s), and/or solubilizing agent(s) and so on. The compositions can also contain other active components, e.g. other drugs for the treatment of itch and/or dermatitis.

In some aspects, the compounds as disclosed herein are formulated into compositions that deliver therapeutically effective drug plasma levels through any route of administration, including oral, rectal, and parenteral administration.

It is to be understood that when the term "administration of compound" or a grammatical variant thereof is used, that both bulk substance and any pharmaceutical or veterinary compositions containing said compound may be considered as appropriate as would be recognized by one skilled in the art.

In certain embodiments, a compound described herein is used in methods of treating or preventing serotonin-, histamine-, chloroquine-, substance P-, compound 48/80 (N-methyl-p-methoxyphenethylamine with formaldehyde)-, dry skin-, herpes zoster-, IL-31-, induced atopic dermatitis-, and bile acid-induced itch in non-human models of itch. These models are expected by someone skilled in the art to predict efficacy for treating itch in human patients. For example, dry skin-induced itch may predict efficacy in uremic pruritus or itch associated with diabetes, or xerosis associated with aging. As a further example, bile-acid induced itch may predict itch associated with cholestasis.

In some embodiments, a compound described herein treats and/or prevents itch and/or dermatitis associated with any form of dermatitis, and atopic dermatitis and contact dermatitis in particular. Animal models expected by someone skilled in the art to predict efficacy for treating itch and/or dermatitis in human patients with dermatitis have been described in Martel et. al. Yale J Biol Med 2017, 90, 389-402.

In one embodiment, the methods described herein are applicable to preventing itch and/or lesions that are associated with seasonal conditions such as seborrheic dermatitis, xerosis, eczema, and atopic eczematous dermatitis. Subjects that have previous episodes of these conditions but currently the symptoms have disappeared. Such subjects are highly susceptible to itch when these conditions do occur again. For example, xerosis is common among the elderly living in temperate climates mainly during the winter months because of the enclosed indoor heating and low humidity during the winter months. Pruritus can also develop as a result of disruption of the epidermal barrier associated with aging leading to inflammation and the release of cysteine proteases, activation of PARs and then the sensation of itch. Similarly, eczema, and atopic eczematous dermatitis tend to "flare up" when there is low humidity and/or during the winter months. Atopic dermatitis is also associated with altered skin barrier function, inflammation and the release of cysteine proteases, activation of PARs and then the sensation of itch. Other examples of seasonal itch include but are not limited to the itch associated with seasonal allergy (also known as hay fever) during the autumn and spring each year. Summer seasonal recurrent dermatitis (SSRD), also known as summer eczema and sweet itch is a skin disease caused by allergic reaction to insect bites. SSRD is considered to be caused by an allergic reaction to the saliva of *Culicoides* flies (also called midges and "no-see-ums"), grass protein, and filariad worm larvae. Sweet itch occurs only in the late spring and summer when insects are present; during the winter months the skin heals and the hair grows back. The therapeutics described herein can be administered during the winter months to the elderly, administered for a subject who has eczema and is temporarily relocating to a dry climate, e.g. vacation, or administered during the seasons when seasonal itch occurs.

In some embodiments, a compound as described herein can be used for treatment and/or prevention of itch and/or lesions resulting from any other skin condition described in LIST 1(a).

In some embodiments, a compound as described herein can be used for treatment of itch associated with the systemic illnesses described in LIST 1 (b-c).

In some embodiments, a compound as described herein treats any remaining form of itch listed in LIST 1 not covered by the previous embodiments.

In some embodiments, the method described herein is used in conjunction with other known anti-itch therapies including, but not limited to, menthol, menthol and phenol, calamine, topical antihistamines, local anesthetics, capsaicin, strontium nitrate, H1-receptor antagonists, H2-receptor antagonists, doxepin, ondansetron, paroxetine, mirtazapine, opioid antagonists, neurontin, NK1-receptor antagonists, PDE-4 inhibitors, and other know therapies for the ailments comprising LIST 1. For example, for dry-skin itch: emollient cream; for cholestasis-related itch: colestyramine, rifampicin, opioid antagonists, and androgens; for uremia-related itch: dialysis, and UVB phototherapy; and for paraneoplasia-related itch: paroxetin.

V. Formulations

In some embodiments, effective concentrations of one or more of the compounds described herein, including any pharmaceutically acceptable salt, solvate, prodrug, hydrate, co-crystal thereof, or derivative thereof, are mixed with a suitable pharmaceutical carrier or vehicle known to those skilled in the art to be suitable for systemic, or regional administration. In some embodiments, the administration is systemic. In one embodiment, regional administration comprises intrathecal and/or intrascalene administration. Compounds are included in a therapeutically effective amount that reduces the pruritic state and/or lesion (especially dermatitis) for which treatment is contemplated. The concentration of active compound in the composition will depend on absorption, inactivation, excretion rates of the active compound, the dosage schedule, and amount administered as well as other factors known to those of skill in the art.

The dosage of the compound as described herein for reducing the pruritic state and/or lesion (i.e. dermatitis) is from about 0.001 to about 100 mg/kg, from about 0.001 to about 90 mg/kg, from about 0.001 to about 80 mg/kg, from about 0.001 to about 70 mg/kg, from about 0.001 to about 60 mg/kg, from about 0.001 to about 50 mg/kg, from about 0.001 to about 40 mg/kg, from about 0.001 to about 30 mg/kg, from about 0.001 to about 20 mg/kg, from about 0.001 to about 10 mg/kg, from about 0.001 to about 5 mg/kg, from about 0.001 to about 1 mg/kg, from about 0.001 to about 0.5 mg/kg, or from about 0.001 to about 0.1 mg/kg, with respect to a body weight of the patient. In some cases, a compound as described herein can be prepared in a unit dose or a fixed form. For example, a unit or fixed dose can include 5, 10, 25, 50, 75, and 100 mg dosage units for administration for 1 to 4 times a day.

In some cases, a dosage of a compound as described herein for reducing the pruritic state and/or lesion (i.e. dermatitis) is from about 0.01 mg to about 200 mg, from about 0.01 mg to about 190 mg, from about 0.01 mg to about 180 mg, from about 0.01 mg to about 170 mg, from about 0.01 mg to about 160 mg, from about 0.01 mg to about 150 mg, from about 0.01 mg to about 140 mg, from about 0.01 mg to about 130 mg, from about 0.01 mg to about 120 mg, from about 0.01 mg to about 110 mg, from about 0.01 mg to about 100 mg, from about 0.01 mg to about 90 mg, from about 0.01 mg to about 80 mg, from about 0.01 mg to about 70 mg, from about 0.01 mg to about 60 mg, from about 0.01 mg to about 50 mg, from about 0.01 mg to about 40 mg, from about 0.01 mg to about 30 mg, from about 0.01 mg to about 20 mg, or from about 0.01 mg to about 10 mg.

In some cases, a dosage can vary depending from compound to compound. In some instances, a dosage for PF-06372865 can be from about 0.01 mg to about 200 mg, from about 0.05 mg to about 200 mg, from about 0.1 to about 200 mg, from about 1 mg to about 200 mg, from about 10 mg to about 200 mg, from about 10 mg to about 150 mg, from about 10 mg to about 100 mg, from about 10 mg to about 75 mg, from about 10 mg to about 50 mg, from about 15 mg to about 100 mg, from about 15 mg to about 75 mg, from about 15 mg to about 50 mg, from about 20 mg to about 100 mg, from about 20 mg to about 75 mg, or from about 20 mg to about 50 mg. In some instances, a dosage for AZD7325 can be from about 0.01 mg to about 100 mg, from about 0.05 mg to about 100 mg, from about 0.1 to about 100 mg, from about 1 mg to about 100 mg, from about 1 mg to about 90 mg, from about 1 mg to about 80 mg, from about 1 mg to about 70 mg, from about 1 mg to about 60 mg, from about 1 mg to about 50 mg, from about 5 mg to about 50 mg, from about 5 mg to about 40 mg, from about 5 mg to about 30 mg, or from about 5 mg to about 20 mg. In some instances, a dosage for SL65.1498 can be from about 0.01 mg to about 100 mg, from about 0.05 mg to about 100 mg, from about 0.1 to about 100 mg, from about 0.5 mg to about 100 mg, from about 0.5 mg to about 90 mg, from about 0.5 mg to about 80 mg, from about 0.5 mg to about 70 mg, from about 0.5 mg to about 60 mg, from about 0.5 mg to about 50 mg, from about 1 mg to about 50 mg, from about 2.5 mg to about 50 mg, from about 2.5 mg to about 45 mg, from about 2.5 mg to about 40 mg, from about 2.5 mg to about 35 mg, from about 2.5 mg to about 30 mg, from about 2.5 mg to about 25 mg, from about 2.5 mg to about 20 mg, from about 5 mg to about 50 mg, from about 5 mg to about 45 mg, from about 5 mg to about 40 mg, from about 5 mg to about 35 mg, from about 5 mg to about 30 mg, from about 5 mg to about 25 mg, or from about 2.5 mg to about 20 mg. In some instances, a dosage for AZD6280 can be from about 0.01 mg to about 100 mg, from about 0.05 mg to about 100 mg, from about 0.1 to about 100 mg, from about 0.5 mg to about 100 mg, from about 1 mg to about 100 mg, from about 5 mg to about 100 mg, from about 5 mg to about 90 mg, from about 5 mg to about 80 mg, from about 5 mg to about 70 mg, from about 5 mg to about 60 mg, from about 5 mg to about 50 mg, from about 5 mg to about 40 mg, from about 5 mg to about 30 mg, from about 5 mg to about 20 mg, from about 10 mg to about 100 mg, from about 10 mg to about 90 mg, from about 10 mg to about 80 mg, from about 10 mg to about 70 mg, from about 10 mg to about 60 mg, from about 10 mg to about 50 mg, from about 10 mg to about 40 mg, from about 10 mg to about 30 mg, from about 10 mg to about 20 mg, from about 20 mg to about 100 mg, from about 20 mg to about 90 mg, from about 20 mg to about 80 mg, from about 20 mg to about 70 mg, from about 20 mg to about 60 mg, from about 20 mg to about 50 mg, or from about 20 mg to about 40 mg.

In some cases, a pharmaceutical composition can be formulated for oral delivery. Oral pharmaceutical dosage forms are either solid or liquid.

Solid oral dosage forms comprise tablets, capsules, granules, oral thin film strips, and bulk powders. Types of oral tablets include compressed tablets which are uncoated, enteric-coated, sugar-coated or film-coated; chewable lozenges/tablets; and tablets that dissolve in the mouth. Capsules comprise hard gelatin, hydroxypropyl methylcellulose, soft gelatin, or other capsule material commonly used in the art. Oral thin-film strips are comprised of one or more fast dissolving hydrophilic polymers some of which have good mucoadhesive properties. Granules and powders may be provided in non-effervescent or effervescent form in combination with other ingredients known to those skilled in the art.

Pharmaceutically acceptable carriers utilized in tablets, capsules, granules and powders comprise binders, lubricants, diluents, disintegrating agents, coloring agents, flavoring agents, and wetting agents as deemed appropriate by one skilled in the art. Enteric-coatings resist the action of stomach acid and dissolve or disintegrate in the neutral or alkaline intestines. Sugar-coated tablets are compressed tablets to which different layers of pharmaceutically acceptable substances may be applied. Film-coated tablets are compressed tablets which have been coated with a water-soluble polymer. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed, chewable tablets, powders and granules. Flavoring and sweetening agents are especially useful in the formation of chewable tablets and lozenges.

Examples of binders include glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Disintegrating agents include corn starch, potato starch, bentonite, methylcellulose, agar and carboxymethyl cellulose. Coloring agents include, for example, any of the approved certified water-soluble FD and C dyes, mixtures thereof, and water insoluble FD and C dyes suspended on alumina hydrate. Sweetening agents include sucrose, lactose, mannitol and artificial sweetening agents such as sodium cyclamate and saccharin, and any number of spray dried flavors. Flavoring agents include natural flavors extracted from plants such as fruits and synthetic blends of compounds which produce a pleasant sensation. Wetting agents include propylene glycol monostearate, sorbitan monooleate, diethylene glycol monolaurate and polyoxyethylene laural ether. Enteric-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

In the preparation of a soft gel capsule, pharmaceutically acceptable adjuvants, excipients and additives are conventionally utilized. Additives include, for example, viscosity regulators (e.g., lecithin, etc.), fragrances (e.g., peppermint oil, lemon oil, etc.), antioxidants (e.g., tocopherol, etc.), preservatives (e.g., parabens, etc.), coloring agents, glycerin, Sorbitol, gelatine, etc. The soft capsule preparation can be prepared according to conventional methods for the preparation of soft capsules.

Oral thin-film strips are designed to wet and dissolve quickly upon contact with saliva and buccal tissue, thereby releasing the contained pharmaceutical components. The main component of these thin films is one or more hydrophilic polymers, some of which have good mucoadhesive properties. In such a case, the wetted polymer strongly adheres to buccal tissue until complete dissolution occurs. Quick dissolution and mucoadhesion are key properties for patient compliance and improved administration of the contained therapeutics.

Liquid oral dosage forms include aqueous solutions, emulsions, suspensions, solutions and/or suspensions reconstituted from non-effervescent granules, and solutions and/or suspensions reconstituted from effervescent granules. Aqueous solutions include, for example, elixirs and syrups. Emulsions are either oil-in water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substance used in effervescent granules, to be reconstituted into a liquid oral dosage form, include organic acids and a source of carbon dioxide. Coloring and flavoring agents may be used in all of the above dosage forms.

Solvents comprise glycerin, sorbitol, ethyl alcohol and syrup. Examples of preservatives comprise glycerin, methyl and propylparaben, benzoic acid, sodium benzoate and alcohol. Examples of non-aqueous liquids utilized in emulsions comprise mineral oil and cottonseed oil. Examples of emulsifying agents comprise gelatin, acacia, tragacanth. bentonite, and surfactants such as polyoxyethylene sorbitan monooleate. Suspending agents comprise sodium carboxymethylcellulose. pectin, tragacanth, Veegum and acacia. Diluents comprise lactose and sucrose. Sweetening agents comprise sucrose, syrups, glycerin and artificial sweetening agents such as sodium cyclamate and saccharin. Wetting agents comprise propylene glycol monostearate, sorbitan monooleate, diethylene glycol monolaurate, and polyoxyethylene lauryl ether. Organic acids comprise citric and tartaric acid. Sources of carbon dioxide comprise sodium bicarbonate and sodium carbonate. Coloring agents comprise any of the approved certified water-soluble FD and C dyes, and mixtures thereof. Flavoring agents comprise natural flavors extracted from plants such fruits, and synthetic blends of compounds which produce a pleasant taste sensation.

In some cases, a pharmaceutical composition can be formulated for rectal delivery. Pharmaceutical dosage forms for rectal administration are rectal suppositories, capsules and tablets for systemic effect, ointments, and creams. In the preferred embodiment, the pharmaceutical dosage form is a rectal suppository. Rectal suppositories, as used herein, means solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point.

Examples of bases comprise cocoa butter (*theobroma* oil), glycerin-gelatin, carbowax. (polyoxyethylene glycol) and appropriate mixtures of mono-, di- and triglycerides of fatty acids. Combinations of the various bases may be used. Agents to raise the melting point of suppositories comprise spermaceti and wax. Rectal suppositories may be prepared either by the compressed method or by molding. The typical weight of a rectal suppository is about 2 to 3 gm. Tablets and capsules for rectal administration are manufactured using the same pharmaceutically acceptable substances and by the same methods as for formulations for oral administration.

In some cases, a pharmaceutical composition can be formulated for parenteral delivery. Parenteral pharmaceutical dosage forms are administered either internally or externally.

Preparations for internal parenteral administration, comprise sterile solutions ready for injection or infusion, sterile dry soluble products ready to be combined with a solvent just prior to use such as hypodermic tablets and lyophilized powders, sterile suspensions ready for injection or infusion, sterile dry insoluble products ready to be combined with a vehicle just prior to use and sterile emulsions. The solutions may be either aqueous or nonaqueous. In addition, any preparation comprising a dry powder blend, solution, emulsion, or suspension that produces a therapeutically effective plasma level upon inhalation, or when applied intranasally or intravaginally (including vaginal suppositories, creams, and ointments) is included. Parenteral preparations can further include any ointment, cream, gel, foam, lotion, emulsion, suspension, solution, medicated bandage, adhesive patch, microneedle patch, nasal spray, eyedrop, dry powder blend, vapor, or aerosol that produces therapeutically effective plasma levels when applied to any part of the body other than the alimentary canal, including but not limited to, the skin, the eyes, the lips, the respiratory tract, and the vagina, and any suspension, emulsion, solution or other formulation delivered by subcutaneous, intramuscular, intraperitoneal, intraarticular, intrathecal, interscalene or intravenous injection/infusion. This includes, but is not limited to, administration by syringe, autoinjector, injection port, intravenous bag, micropump, or implanted device/product.

Pharmaceutically acceptable carriers used in injectable or infusible preparations comprise aqueous vehicles, nonaqueous vehicles, antimicrobial agents, isotonic agents, buffers. antioxidants. local anesthetics, suspending and dispersing agents, emulsifying agents, sequestering or chelating agents and other pharmaceutically acceptable substances. Examples of aqueous vehicles comprise Sodium Chloride Injection, Ringers Injection, Isotonic Dextrose Injection, Sterile Water Injection, Dextrose and Lactated Ringers Injection. Nonaqueous parenteral vehicles comprise fixed oils of vegetable origin, cottonseed oil, corn oil, sesame oil and peanut oil. Antimicrobial agents in bacteriostatic or fungistatic concentrations must be added to parenteral preparations packaged in multiple-dose containers which comprise phenols or cresols, mercurials. benzyl alcohol, chlorobutanol, methyl and propyl p-hydroxybenzoic acid esters, thimerosal, benzalkonium chloride and benzethonium chloride. Isotonic agents comprise sodium chloride and dextrose. Buffers comprise phosphate and citrate. Antioxidants comprise sodium bisulfate. Local anesthetics comprise procaine hydrochloride. Suspending and dispersing agents include sodium carboxymethylcellulose, hydroxypropyl methylcellulose, 2-hydroxypropyl-beta-cyclodextrin, and polyvinylpyrrolidone. Emulsifying agents comprise Polysorbate 80 (Tween 80). A sequestering or chelating agent of metal ions comprise EDTA. Pharmaceutical carriers also comprise ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

In some cases, a pharmaceutical composition in injectable form can be formulated as a unit dose. The unit-dose injectable preparations are packaged in an ampoule, vial, syringe, or bag.

All preparations for administration by injection or infusion must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Preparations for external parenteral administration comprise medicated adhesive patches, adhesive patches with dissolving medicated microneedles, creams, ointments, gels, and lotions. In the preferred embodiment, said preparations are medicated adhesive patches or adhesive patches with dissolving medicated microneedles.

Patches containing an array of micron-scale needles which encapsulate a compound as described herein, may produce a therapeutically effective systemic dose when applied to the skin. The needles dissolve within the skin providing either a bolus or sustained delivery of active ingredient depending on the design. These devices are prepared from a wide range of materials such as sugars and polymers. Methods of preparing dissolving microneedles are known to those skilled in the art and comprise micromolding, photopolymerization, drawing lithography and droplet-airborne blowing.

A medicated adhesive patch is comprised of a surface layer, an adhesive layer, and a removable protective layer.

The term "surface layer" as used herein refers to any layer that represents the surface layer after the application of the pharmaceutical patch. This definition includes permanent backing layer commonly used for pharmaceutical patches as well as thin non-removable films that are typically used in thin flexible patches. The surface layer comprises one or more polymers selected from the group consisting of polyurethanes, polyester elastomers, polyether block amides, polyacrylates, ethylene vinyl acetates, ethylene acrylate copolymers, ionomer resins, polyvinyl chloride, polyvinylidene chloride, polyesters and polyolefins, such as polyethylene; polyolefins, in particular polyethylene, polyesters, ethylene vinylacetate copolymers, and polyurethanes are particularly preferred. The surface layer may be a laminate, preferably comprising a polymer film, such as a polyester film, and aluminum foil and/or heat seal layer. The thickness of the surface layer is not particularly limited. Preferably, the surface layer has a thickness within the range of from 0.1 to 5000 µm. In a preferred embodiment, the surface layer has a thickness within the range of from 0.5 to 1000 µm, more preferably from 1 to 750 µm, still more preferably from 5 to 500 µm, most preferably from 10 to 250 µm, and in particular from 20 to 150 µm or from 40 to 100 µm.

The removable protective layer comprises a polymer film and a silicone coating or fluoropolymer coating. Preferably, the polymer film is a polyolefin, in particular polyethylene or polypropylene film or polyester, in particular polyethylene terephthalate film. In a preferred embodiment, the removable protective layer is a silicone coated polyolefin or silicone coated polyester film, such as a silicone coated polyethylene terephthalate, polypropylene or polyethylene film. In another preferred embodiment, the removable protective layer is a fluoropolymer coated polyolefin or polyester film, such as a fluoropolymer coated polyethylene terephthalate, polypropylene or polyethylene film.

The thickness of the removable protective layer is not particularly limited. Preferably, the removable protective layer has a thickness within the range of from 0.1 to 500 µm. In a preferred embodiment, the removable protective layer has a thickness within the range of from 0.5 to 400 µm, more preferably from 1 to 300 µm, still more preferably from 5 to 250 µm, most preferably from 10 to 200 µm, and in particular from 20 to 150 µm or from 40 to 100 µm.

The pharmaceutical patch may contain at least one drug layer, which comprises at least a portion of the total amount of the pharmacologically active ingredient that is contained in the pharmaceutical patch. Preferably, the drug layer comprises at least 10 wt. %, more preferably at least 25 wt. %, still more preferably at least 50 wt. %, yet more preferably at least 75 wt-%, even more preferably at least 85 wt. %, most preferably at least 90 wt. %, and in particular at least 95 wt. % of the total amount of the pharmacologically active ingredient that is contained in the pharmaceutical patch. In an especially preferred embodiment, the drug layer comprises the total amount of the pharmacologically active ingredient that is contained in the pharmaceutical patch. A skilled person recognizes that when the drug layer is not identical with the adhesive layer, a certain amount of the pharmacologically active ingredient migrates from the drug layer into the adjacent drug permeable layer(s) for thermodynamic reasons until an equilibrium has been reached. Thus, even if the material forming the adhesive layer did not contain any pharmacologically active ingredient when the pharmaceutical patch was manufactured, the final product typically does contain pharmacologically active ingredient not only in the drug layer but also in the adhesive layer. The drug layer may be separated from the adhesive layer by a membrane or may be in intimate contact with, i.e. adjacent to the adhesive layer.

The adhesive layer comprises a pressure sensitive adhesive selected from the group consisting of polysilicone-based pressure sensitive adhesives, polyacrylate based pressure sensitive adhesives, polyisobutylene based pressure sensitive adhesives, and styrenic rubber based pressure sensitive adhesives. The thickness of the adhesive layer is not particularly limited and may depend upon a number of factors such as function within the patch (e.g. drug-in-adhesive), content of pharmacologically active ingredient and excipients, prescribed duration of application of pharmaceutical patch on the skin, and the like. Preferably, the adhesive layer has a thickness within the range of from 1.0 to 1000 µm.

In addition, one or more percutaneous penetration enhancers may be included. Percutaneous penetration enhancers comprise:

a) sulfoxides such as dimethylsulfoxide (DMSO) and decylmethylsulfoxide;

b) ethers such as diethylene glycol monoethyl ether (transcutol) and diethylene glycol monomethyl ether;

c) surfactants such as sodium laurate, sodium lauryl sulfate, cetyltrimethylammonium bromide, benzalkonium chloride, poloxamers, polysorbates (e.g. polysorbate 80) and lecithin;

d) 1-substituted azacycloheptan-2-ones such as 1-n-dodecylcyclazacycloheptan-2-one; e) alcohols and fatty alcohols such as ethanol, propanol, octanol, dodecanol, oleyl alcohol, benzyl alcohol, and the like;

f) polyols, esters of polyols and ethers of polyols such as propylene glycol, ethylene glycol, diethylene glycol, dipropylene glycol, glycerol, butanediol, polyethylene glycol, polyvinyl alcohol, triacetine, and polyethylene glycol monolaurate;

g) organic acids such as salicylic acid and salicylates, citric acid, levulinic acid, caprylic acid and succinic acid; as well as dicarboxylic acids and their esters such as dibutylene sebacate;

h) fatty acids such as lauric acid, oleic acid and valeric acid; fatty acid esters such as isopropyl myristate, isopropyl palmitate, methylpropionate, propylene glycol monolaureate, lauryl lactate, oleyl oleate and ethyl oleate;

i) amides and other nitrogenous compounds such as urea, dimethylacetamide, dimethylformamide, 2-pyrrolidone, 1-methyl-2-pyrrolidone, ethanolamine, diethanolamine, triethanolamine and laurocapram (Azone®);

j) terpenes;

k) alkanones;

l) other oligomers or polymers; and mixtures of any of the foregoing.

Formulations comprising a compound as described herein may be included with other aforementioned active compounds to obtain desired combinations of properties.

The compounds of Formulas I, II, III and IV are administered orally, parenterally or rectally in unit-dosage forms or multiple-dosage forms. Unit-dose forms, as used herein, refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms includes ampoules, syringes, and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms comprise vials, bottles of tablets or capsules, or bottles of pint or gallons. Hence, multiple dose form is a multiple of unit-doses which are not segregated in packaging.

VI. Examples

The following examples set forth methods in accordance with the disclosure. It is to be understood, however, that these examples are provided by way of illustration and nothing therein should be taken as a limitation upon the overall scope of the disclosure.

Example 1—Effect of PF-06372865 on Chloroquine Induced Itch Model in Male C57BL/6 Mice PF-06372865 was evaluated as an antipruritic and/or antidermatitis agent using a Chloroquine Induced Itch Model in male C57BL/6 mice.

Male C57BL/6 Mice (8-10 weeks) were used in the study. Animals were procured from CRL, Hylasco (CPSCEA registered animal supplier).

Mice were housed one per cage and maintained at controlled environmental conditions with 12-h light and dark cycles. The temperature and humidity of the room were maintained between 22±3° C. and 55±5%, respectively. The maximum and minimum temperature and relative humidity in the experimental rooms were recorded once daily.

NCT10004 Phosphate (Standard Compound) Formulation Preparation:

NCT10004 phosphate (adjusted with salt correction factor) was weighed into a clean glass container. 0.5% Methyl Cellulose (MC) was added, and the resulting mixture was mixed well using mild vortexing and stirred for 40 minutes to provide a homogeneous suspension.

| NCT10004 (mg/kg) | NCT10004 quantity weighed (mg) | 0.5% Methyl Cellulose (mL) |
|---|---|---|
| 3 | 3.76 | 10 |

PF-06372865 (Test Compound) Formulation Preparation:

PF-06372865 was weighed into a clean mortar. Liquefied Solutol (i.e., Polyoxyl 15 Hydroxystearate) was added drop wise and triturated using a pestle for 2-3 minutes, then Glycerol formal was added and mixed in same fashion. The volume was made up by slowly adding the required volume of water. The resulting mixture was mixed well using mild vortexing to provide a homogeneous suspension. (Details in below chart)

| PF-06372865 Dose (mg/kg) | PF-06372865 quantity weighed (mg) | 17% Solutol (mL) | 18% Glycerol Formal (mL) | 65% water (mL) | Total Volume Prepared (mL) |
|---|---|---|---|---|---|
| 30 | 12.6 | 0.714 | 0.756 | 2.73 | 4.2 |
| 10 | 6 | 1.02 | 1.08 | 3.9 | 6 |
| 3 | 2.4 | 1.36 | 1.44 | 5.20 | 8 |
| 1 | Formulation prepared by diluting stock of 10 mg/kg dose | | | | |
| 0.3 | Formulation prepared by diluting stock of 3 mg/kg dose | | | | |

Chloroquine Phosphate (CQ) Preparation:

27 mg of chloroquine phosphate was weighed in a clean glass container. 6 mL PBS was added, and the resulting mixture was mixed well using mild vortexing to form the desired strength solution.

Treatment Groups:

| Group No. | Treatment Group (n = 9 per group) |
|---|---|
| 1 | Vehicle, (10 ml/kg) 17% Solutol/ 18% glycerol formal/65% water |
| 2 | PF-06372865, 0.3 mg/kg, PO |
| 3 | PF-06372865, 1 mg/kg, PO |
| 4 | PF-06372865, 3 mg/kg, PO |
| 5 | PF-06372865, 10 mg/kg, PO |
| 6 | PF-06372865, 30 mg/kg, PO |
| 7 | NCT10004 Phosphate, 3 mg/kg, PO (0.5% Methyl Cellulose) |

Experimental Procedure:

The right-side cheek area of all the animals was shaved with animal clippers 1 day prior to the experiment. Animals were randomized into different treatment groups (n=9/group) based on body weight to avoid variability in weights across groups. NCT10004 Phosphate and PF-06372865 formulations and chloroquine phosphate solution were prepared on the day of the experiment.

Animals were dosed per oral with respective treatment group using a dose volume of 10 ml/kg. Times of dosing were recorded. Immediately after compound treatment, animals were kept in an empty transparent chamber (23 cm length×17 cm width) for acclimatization and observation.

Ninety (90) minutes post compound dosing, 50-µl of chloroquine phosphate solution (a 200-µg dose) was injected intracutaneously into the animal's right cheek. Animals were returned to the same chamber for observation. Animals were observed by an observer blind to the treatment group for a period of 30 minutes post chloroquine injection. Total number of bouts of scratching directed at the ipsilateral cheek were recorded for 30 minutes.

Figure 1B:
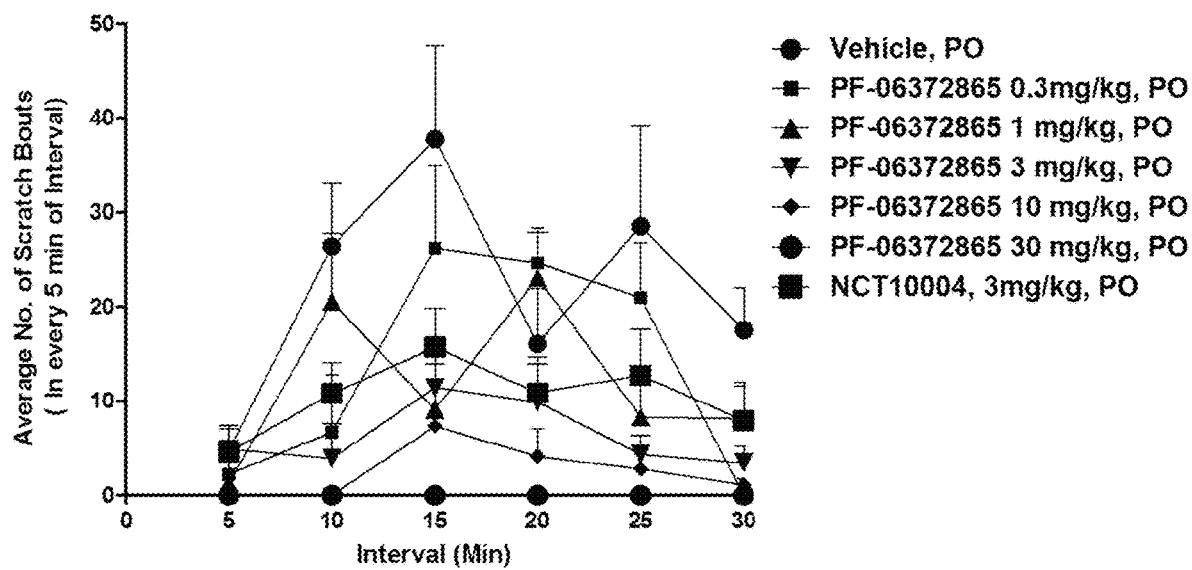

Results:

PF-06372865 treatment showed dose dependent decrease in total number of scratching bouts, quantified for 30 minutes post CQ injection (FIG. 1A). Statistically significant decrease in scratching bouts were observed in PF-06372865 treatment groups at 0.3, 1, 3, 10 and 30 mg/kg doses compared to vehicle treatment. The number of scratching bouts across each 5 minute time interval is presented in FIG. 1B and Table 1.

TABLE 1

Effect of PF-06372865 on Chloroquine-Induced Itch Model in Male C57BL/6 Mice

| Treatment Group | Animal ID | Scratching bouts (Nos.) in 30 min | | | | | | Total Scratching bouts (Nos./30 min) |
|---|---|---|---|---|---|---|---|---|
| | | 0-5 min | 5-10 min | 10-15 min | 15-20 min | 20-25 min | 25-30 min | |
| Vehicle, (10 ml/kg) 17% Solutol/18% glycerol format/65% water | 1 | 0 | 6 | 9 | 24 | 0 | 4 | 43 |
| | 2 | 15 | 15 | 18 | 14 | 24 | 18 | 104 |
| | 3 | 0 | 60 | 92 | 0 | 65 | 0 | 217 |
| | 4 | 0 | 0 | 44 | 11 | 88 | 36 | 179 |
| | 5 | 12 | 33 | 47 | 14 | 40 | 23 | 169 |
| | 6 | 0 | 32 | 14 | 56 | 4 | 0 | 106 |
| | 7 | 0 | 52 | 70 | 0 | 36 | 25 | 183 |
| | 8 | 15 | 20 | 3 | 23 | 0 | 21 | 82 |
| | 9 | 0 | 20 | 43 | 3 | 0 | 31 | 97 |
| | MEAN | 467 | 26.44 | 37.78 | 16.11 | 28.56 | 17.56 | 131.11 |
| | SEM | 2.35 | 6.65 | 9.95 | 5.81 | 10.62 | 4.44 | 19.19 |
| | N | 9 | 9 | 9 | 9 | 9 | 9 | 9 |
| PF-06372865, 0.3 mg/kg, PO | 10 | 0 | 56 | 47 | 10 | 0 | 0 | 113 |
| | 11 | 0 | 0 | 0 | 25 | 49 | 0 | 74 |
| | 12 | 0 | 0 | 0 | 25 | 0 | 0 | 25 |
| | 13 | 0 | 0 | 0 | 39 | 33 | 0 | 72 |
| | 14 | 0 | 1 | 19 | 13 | 0 | 0 | 33 |
| | 15 | 1 | 0 | 46 | 36 | 27 | 0 | 110 |
| | 16 | 15 | 0 | 76 | 31 | 27 | 0 | 149 |

TABLE 1-continued

Effect of PF-06372865 on Chloroquine-Induced Itch Model in Male C57BL/6 Mice

| Treatment Group | Animal ID | Scratching bouts (Nos.) in 30 min | | | | | | Total Scratching bouts (Nos./30 min) |
|---|---|---|---|---|---|---|---|---|
| | | 0-5 min | 5-10 min | 10-15 min | 15-20 min | 20-25 min | 25-30 min | |
| | 17 | 0 | 0 | 21 | 11 | 24 | 0 | 56 |
| | 18 | 4 | 3 | 27 | 32 | 29 | 0 | 95 |
| | MEAN | 2.22 | 6.67 | 26.22 | 24.67 | 21.00 | 0.00 | 80.78 |
| | SEM | 1.66 | 6.18 | 8.70 | 3.66 | 5.77 | 0.00 | 13.37 |
| | N | 9 | 9 | 9 | 9 | 9 | 9 | 9 |
| PF-06372865, 1 mg/kg, PO | | 0 | 22 | 9 | 41 | 28 | 6 | 106 |
| | | 0 | 0 | 0 | 14 | 0 | 25 | 39 |
| | | 0 | 18 | 13 | 28 | 18 | 4 | 81 |
| | | 1 | 0 | 1 | 16 | 8 | 0 | 26 |
| | | 0 | 13 | 0 | 45 | 21 | 14 | 93 |
| | | 8 | 62 | 0 | 25 | 0 | 0 | 95 |
| | | 2 | 49 | 9 | 11 | 0 | 0 | 71 |
| | | 0 | 18 | 4 | 0 | 0 | 0 | 22 |
| | | 0 | 3 | 46 | 28 | 0 | 24 | 101 |
| | MEAN | 1.22 | 20.56 | 9.11 | 23.11 | 8.33 | 8.11 | 70.44 |
| | SEM | 0.88 | 7.22 | 4.88 | 4.81 | 3.70 | 3.45 | 11.01 |
| | N | 9 | 9 | 9 | 9 | 9 | 9 | 9 |
| PF-06372865, 3 mg/kg, PO | | 16 | 0 | 44 | 17 | 13 | 9 | 99 |
| | | 0 | 0 | 4 | 14 | 0 | 0 | 18 |
| | | 0 | 33 | 0 | 33 | 0 | 0 | 66 |
| | | 19 | 0 | 10 | 0 | 0 | 0 | 29 |
| | | 0 | 2 | 16 | 3 | 0 | 3 | 24 |
| | | 1 | 0 | 29 | 0 | 14 | 15 | 59 |
| | | 3 | 0 | 0 | 0 | 0 | 0 | 3 |
| | | 5 | 0 | 0 | 0 | 3 | 4 | 12 |
| | | 0 | 0 | 0 | 22 | 9 | 0 | 31 |
| | MEAN | 4.89 | 3.89 | 11.44 | 9.89 | 4.33 | 3.44 | 37.89 |
| | SEM | 2.46 | 3.65 | 5.23 | 4.06 | 1.99 | 1.76 | 10.26 |
| | N | 9 | 9 | 9 | 9 | 9 | 9 | 9 |
| PF-06372865, 10 mg/kg, PO | | 0 | 0 | 0 | 0 | 0 | 2 | 2 |
| | | 0 | 0 | 0 | 0 | 12 | 2 | 14 |
| | | 0 | 0 | 33 | 8 | 0 | 0 | 41 |
| | | 0 | 0 | 33 | 0 | 0 | 0 | 33 |
| | | 0 | 0 | 0 | 0 | 0 | 0 | 0 |
| | | 0 | 0 | 0 | 0 | 9 | 6 | 15 |
| | | 0 | 0 | 0 | 3 | 0 | 0 | 3 |
| | | 0 | 0 | 0 | 26 | 4 | 0 | 30 |
| | MEAN | 0.00 | 0.00 | 7.33 | 4.11 | 2.78 | 1.11 | 15.33 |
| | SEM | 0.00 | 0.00 | 4.85 | 2.88 | 1.54 | 0.68 | 5.25 |
| | N | 9 | 9 | 9 | 9 | 9 | 9 | 9 |
| PF-06372865, 30 mg/kg, PO | | 0 | 0 | 0 | 0 | 0 | 0 | 0 |
| | | 0 | 0 | 0 | 0 | 0 | 0 | 0 |
| | | 0 | 0 | 0 | 0 | 0 | 0 | 0 |
| | | 0 | 0 | 0 | 0 | 0 | 0 | 0 |
| | | 0 | 0 | 0 | 0 | 0 | 0 | 0 |
| | | 0 | 0 | 0 | 0 | 0 | 0 | 0 |
| | | 0 | 0 | 0 | 0 | 0 | 0 | 0 |
| | | 0 | 0 | 0 | 0 | 0 | 0 | 0 |
| | | 0 | 0 | 0 | 0 | 0 | 0 | 0 |
| | MEAN | 0.00 | 0.00 | 0.00 | 0.00 | 0.00 | 0.00 | 0.00 |
| | SEM | 0.00 | 0.00 | 0.00 | 0.00 | 0.00 | 0.00 | 0.00 |
| | N | 9 | 9 | 9 | 9 | 9 | 9 | 9 |
| NCT10004, 3 mg/kg, PO (0.5% Methyl Cellulose) | | 4 | 6 | 21 | 0 | 47 | 0 | 78 |
| | | 0 | 14 | 12 | 0 | 17 | 32 | 75 |
| | | 10 | 0 | 1 | 8 | 3 | 0 | 22 |
| | | 10 | 8 | 8 | 21 | 11 | 0 | 58 |
| | | 0 | 22 | 0 | 0 | 0 | 0 | 22 |
| | | 7 | 31 | 14 | 24 | 0 | 18 | 94 |
| | | 1 | 1 | 31 | 27 | 4 | 21 | 85 |
| | | 5 | 9 | 21 | 0 | 17 | 0 | 52 |
| | | 4 | 6 | 34 | 18 | 16 | 0 | 78 |
| | MEAN | 4.56 | 10.78 | 15.78 | 10.89 | 12.78 | 7.89 | 62.67 |
| | SEM | 1.29 | 3.36 | 4.02 | 3.85 | 4.89 | 4.13 | 8.78 |
| | N | 9 | 9 | 9 | 9 | 9 | 9 | 9 |

A dose dependent increase in sedation was observed in PF-06372865 treatment groups at 10 mg/kg and 30 mg/kg treatment NCT10004 (Positive control) group showed 53% decrease in scratching bouts compared to vehicle treatment.

Dose dependent increase in sedation was observed in PF-06372865 treatment groups at 10 mg/kg and 30 mg/kg treatment Minimal sedation was observed at PF-06372865, 3 mg/kg treatment group. No other behavioral change or clinical sign were observed in any of the PF-06372865 treatment groups. No behavioral change or any clinical signs were observed in NCT10004 treatment group.

These experiments demonstrate that PF-06372865 is suitable antipruritic agent for treatment of human patients, as shown by efficacy of PF-06372865 in decreasing scratching bouts in the Chloroquine-Induced Itch Model.

Example 2—Effect of AZD7325 on Chloroquine Induced Itch Model

Other GABAA positive allosteric modulators are predicted to have similar effects on pruritic conditions and dermatitis as PF-06372865. To demonstrate the broad efficacy of GABAA receptor modulators compounds, AZD7325 was screened for its suitability as an antipruritic and/or anti-dermatitis agent following a similar protocol as described in Example 2. In this study, the efficacy of AZD7325 was evaluated in the Chloroquine Induced Itch Model in Male C57BL/6 Mice.

NCT10004 Phosphate (Standard Compound) Formulation Preparation:

A 3 mg/kg stock of NCT10004 phosphate (adjusted with salt correction factor) was prepared by weighing 3.80 mg into a clean glass container. 10 mL of 0.5% Methyl Cellulose (MC) was added, and the resulting mixture was mixed well using mild vortexing and stirred for 40 minutes to provide a homogeneous suspension.

AZD7325 (Test Compound) Formulation Preparation:

AZD7325 was weighed into a clean glass container. A 5% 2-hydroxypropyl-β-cyclodextrin was added and the resulting mixture was mixed well using mild vortexing and sonicated for 15-20 minutes to provide a homogeneous suspension.

| AZD7325 Dose (mg/kg) | AZD7325 quantity weighed (mg) | 5% 2-hydroxypropyl-β-cyclodextrin volume added (ml) |
|---|---|---|
| 30 | 9.6 | 3.2 |
| 10 | 4.4 | 4.4 |
| 3 | 3.2 | 10.66 |
| 1 | Formulation prepared by diluting stock of 10 mg/kg dose | |
| 0.3 | Formulation prepared by diluting stock of 3 mg/kg dose | |

Chloroquine Phosphate (CQ) Preparation:

21 mg of chloroquine phosphate was weighed in a clean glass container. 5.2 mL PBS was added, and the resulting mixture was mixed well using mild vortexing to form the desired strength solution.

Treatment Groups:

| Group No. | Treatment Group (n = 9 per group) |
|---|---|
| 1 | Vehicle, (10 ml/kg) 5% 2-hydroxypropyl-β-cyclodextrin |
| 2 | AZD7325, 0.3 mg/kg, PO |
| 3 | AZD7325, 1 mg/kg, PO |
| 4 | AZD7325, 3 mg/kg, PO |
| 5 | AZD7325, 10 mg/kg, PO |
| 6 | AZD7325, 30 mg/kg, PO |
| 7 | NCT10004 Phosphate, 3 mg/kg, PO (0.5% Methyl Cellulose) |

Experimental Procedure

The right-side cheek area of all the animals was shaved with animal clippers 1 day prior to the experiment. Animals were randomized into different treatment groups based on body weight to avoid variability in weights across groups one day prior to experiment. Reference formulations and chloroquine phosphate solution were prepared on the day of the experiment.

Animals were dosed per oral with respective treatment group using a dose volume of 10 ml/kg. Times of dosing were recorded. Immediately after compound treatment, animals were kept in a empty transparent chamber (23 cm length×17 cm width) for acclimatization and observation.

Ninety (90) minutes post compound dosing, 50-µl of chloroquine phosphate solution (a 200-µg dose) was injected intracutaneously into the animal's right cheek. Animals were returned to the same chamber for observation. Animals were observed by an observer blind to the treatment group for a period of 30 minutes post chloroquine injection. Total number of bouts of scratching directed at the ipsilateral cheek were recorded for 30 minutes.

Figure 2A:
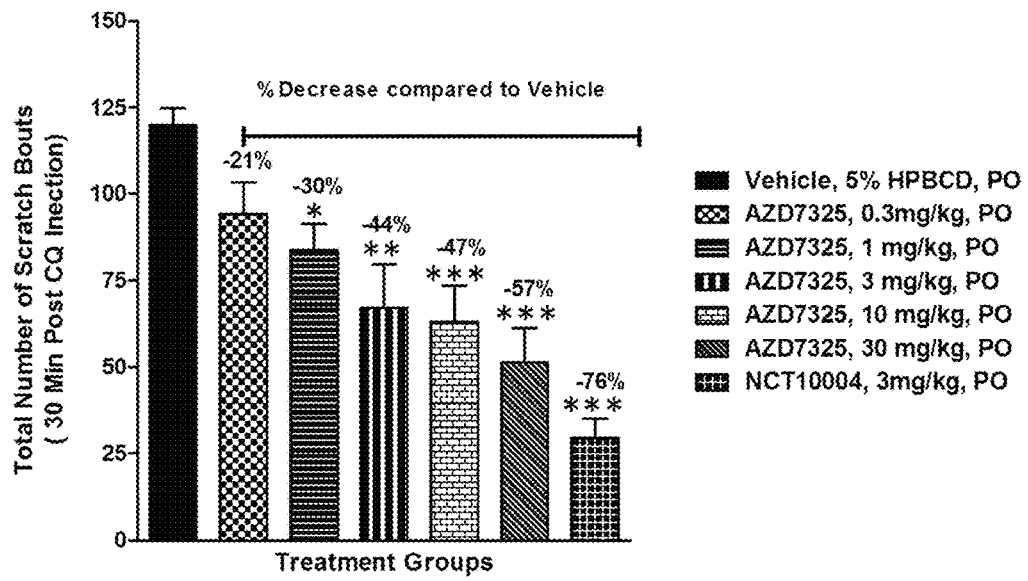
FIGS. 2A-2B depict the effect of AZD7325 on a Chloroquine (CQ)-Induced Itch Model in Male C57BL/6 Mice. Data is represented as Mean±SEM, (n=6 animals/group/time point).
Figure 2B:
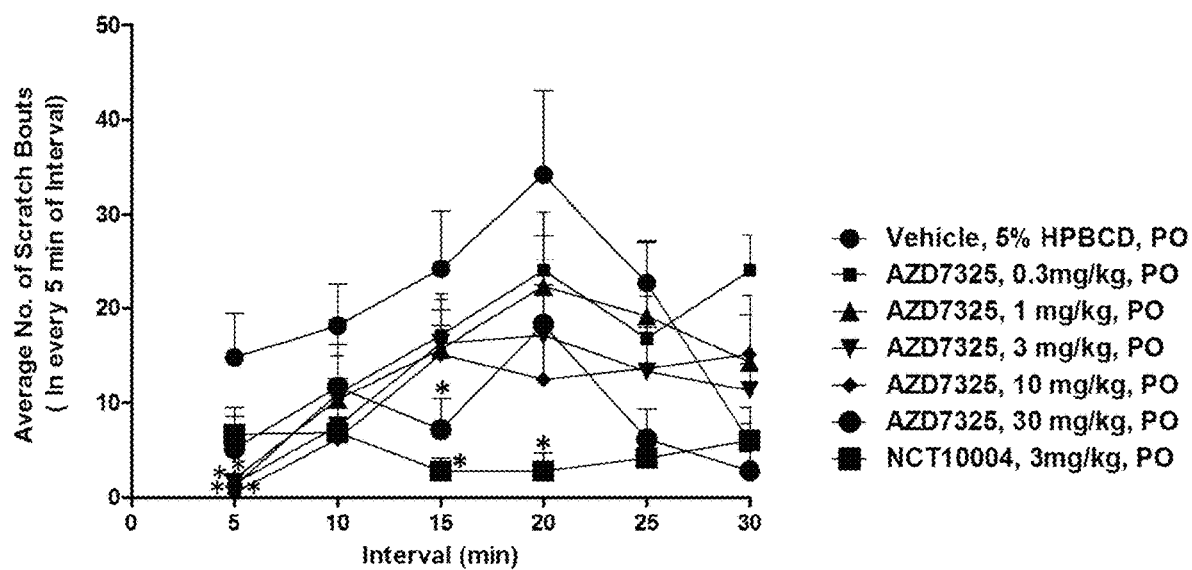

Results:

AZD7325 treatment showed a dose dependent decrease in total number of scratching bouts, quantified for 30 minutes post CQ injection (FIG. 2A). Statistically significant decrease in scratching bouts were observed in AZD7325 treatment groups at 1, 3, 10 and 30 mg/kg doses compared to vehicle treatment. NCT10004 (Positive control) group showed 76% decrease in scratching bouts compared to vehicle treatment. The number of scratching bouts across each 5 minute time interval is presented in FIG. 2B and Table 2.

TABLE 2

Effect of AZD7325 on Chloroquine-Induced Itch Model in Male C57BL/6 Mice

| Treatment Group | Animal ID | Scratching bouts (Nos.) In 30 min | | | | | | Total Scratching bouts (Nos.)/30 min |
|---|---|---|---|---|---|---|---|---|
| | | 0-5 min | 5-10 min | 10-15 min | 15-20 min | 20-25min | 25-30 min | |
| Vehicle 5% 2-Hydroxypropyl-β-cyclodextrin (10 ml/kg) | 1 | 13 | 15 | 19 | 23 | 32 | 19 | 121 |
| | 2 | 31 | 20 | 25 | 18 | 9 | 0 | 103 |
| | 3 | 25 | 0 | 19 | 34 | 28 | 16 | 122 |
| | 4 | 10 | 21 | 13 | 53 | 11 | 0 | 108 |
| | 5 | 0 | 33 | 54 | 10 | 36 | 0 | 133 |
| | 6 | 10 | 20 | 15 | 67 | 0 | 0 | 112 |
| | MEAN | 14.83 | 18.17 | 24.17 | 34.17 | 19.33 | 5.83 | 116.50 |
| | SEM | 4.60 | 4.38 | 6.2 | 8.95 | 5.95 | 3.71 | 4.46 |
| | N | 6 | 6 | 6 | 6 | 6 | 6 | 6 |
| AZD7325, 0.3 mg/kg, PO | 7 | 0 | 17 | 22 | 45 | 11 | 21 | 116 |
| | 8 | 0 | 0 | 25 | 30 | 28 | 15 | 98 |
| | 9 | 5 | 9 | 10 | 0 | 18 | 31 | 73 |

TABLE 2-continued

Effect of AZD7325 on Chloroquine-Induced Itch Model in Male C57BL/6 Mice

| Treatment Group | Animal ID | Scratching bouts (Nos.) In 30 min | | | | | | Total Scratching bouts (Nos.)/30 min |
|---|---|---|---|---|---|---|---|---|
| | | 0-5 min | 5-10 min | 10-15 min | 15-20 min | 20-25min | 25-30 min | |
| | 10 | 0 | 24 | 15 | 14 | 29 | 23 | 105 |
| | 11 | 2 | 0 | 1 | 28 | 15 | 15 | 61 |
| | 12 | 0 | 16 | 30 | 27 | 0 | 39 | 112 |
| | MEAN | 1.17 | 11.00 | 17.17 | 24.00 | 16.83 | 24.00 | 94.17 |
| | SEM | 0.83 | 3.98 | 4.35 | 6.27 | 4.45 | 3.86 | 9.08 |
| | N | 6 | 6 | 6 | 6 | 6 | 6 | 6 |
| AZD7325, 1 mg/kg, PO | 13 | 0 | 1 | 0 | 30 | 48 | 0 | 79 |
| | 14 | 2 | 7 | 15 | 24 | 38 | 9 | 95 |
| | 15 | 3 | 18 | 26 | 14 | 7 | 17 | 85 |
| | 16 | 0 | 36 | 8 | 7 | 10 | 4 | 65 |
| | 17 | 6 | 0 | 21 | 44 | 12 | 30 | 113 |
| | 18 | 1 | 0 | 24 | 15 | 0 | 26 | 66 |
| | MEAN | 2.00 | 10.33 | 15.67 | 22.33 | 19.17 | 14.33 | 83.83 |
| | SEM | 0.93 | 5.86 | 4.12 | 5.44 | 7.82 | 4.93 | 7.47 |
| | N | 6 | 6 | 6 | 6 | 6 | 6 | 6 |
| AZD7325, 3 mg/kg, PO | 19 | 3 | 0 | 20 | 18 | 2 | 8 | 51 |
| | 20 | 0 | 0 | 22 | 5 | 32 | 19 | 78 |
| | 21 | 6 | 31 | 17 | 35 | 22 | 8 | 119 |
| | 22 | 0 | 12 | 9 | 26 | 6 | 11 | 64 |
| | 23 | 0 | 0 | 14 | 19 | 10 | 20 | 63 |
| | 24 | 0 | 2 | 16 | 0 | 8 | 2 | 28 |
| | MEAN | 1.50 | 7.50 | 16.33 | 17.17 | 13.33 | 11.33 | 67.17 |
| | SEM | 1.02 | 5.07 | 1.87 | 5.30 | 4.64 | 2.85 | 12.42 |
| | N | 6 | 6 | 6 | 6 | 6 | 6 | 6 |
| AZD7325, 10 mg/kg, PO | 25 | 0 | 7 | 41 | 9 | 0 | 23 | 80 |
| | 26 | 0 | 7 | 11 | 0 | 10 | 37 | 65 |
| | 27 | 0 | 0 | 7 | 22 | 20 | 24 | 73 |
| | 28 | 0 | 22 | 19 | 25 | 19 | 0 | 85 |
| | 29 | 1 | 1 | 0 | 19 | 33 | 7 | 61 |
| | 30 | 2 | 0 | 13 | 0 | 0 | 0 | 15 |
| | MEAN | 0.50 | 6.17 | 15.17 | 12.50 | 13.67 | 15.17 | 63.17 |
| | SEM | 0.34 | 3.44 | 5.78 | 4.52 | 5.26 | 6.17 | 10.30 |
| | N | 6 | 6 | 6 | 6 | 6 | 6 | 6 |
| AZD7325, 30 mg/kg, PO | 31 | 0 | 9 | 8 | 29 | 5 | 0 | 51 |
| | 32 | 1 | 15 | 1 | 0 | 0 | 12 | 29 |
| | 33 | 20 | 0 | 22 | 11 | 16 | 0 | 69 |
| | 34 | 0 | 0 | 3 | 10 | 0 | 5 | 18 |
| | 35 | 0 | 1 | 9 | 47 | 0 | 0 | 57 |
| | 36 | 10 | 45 | 0 | 13 | 16 | 0 | 84 |
| | MEAN | 5.17 | 11.67 | 7.17 | 18.33 | 6.17 | 2.83 | 51.33 |
| | SEM | 3.37 | 7.11 | 3.32 | 6.89 | 3.21 | 2.01 | 10.04 |
| | N | 6 | 6 | 6 | 6 | 6 | 6 | 6 |
| NCT10004, 3 mg/kg, PO (0.5% Methyl Cellulose) | 37 | 16 | 6 | 0 | 0 | 1 | 1 | 24 |
| | 38 | 15 | 0 | 7 | 7 | 4 | 2 | 35 |
| | 39 | 5 | 1 | 0 | 10 | 0 | 8 | 24 |
| | 40 | 2 | 0 | 0 | 0 | 4 | 5 | 11 |
| | 41 | 2 | 0 | 4 | 0 | 16 | 7 | 29 |
| | 42 | 0 | 34 | 6 | 0 | 0 | 13 | 53 |
| | MEAN | 6.67 | 6.83 | 2.83 | 2.83 | 4.17 | 6.00 | 29.33 |
| | SEM | 2.87 | 5.52 | 1.33 | 1.83 | 2.48 | 1.79 | 5.73 |
| | N | 6 | 6 | 6 | 6 | 6 | 6 | 6 |

These experiments demonstrate that the efficacy of PF-06372865 in treating pruritic conditions and dermatitis is also seen in other GABAA positive allosteric modulators such as AZD7325.

Example 3—Effect of PF-06372865 on Histamine-Induced Itch Model in Male C57BL/6 Mice PF-06372865 (an alpha 2, alpha 3, and alpha 5 agonist; and an alpha 1 antagonist) is assessed for its antipruritic effects against a cheek injection of 100 μg histamine in wild-type C57BL/6 mice. The mice are dosed with PF-06372865 by oral gavage ninety (90) minutes before histamine injection. Doses of PF-06372865 are vehicle, 1, 3, 10, 30 and 100 mg/kg. A dose-dependent reduction of scratching bouts is demonstrated by PF-06372865 treatment against histaminergic itch showing that PF-06372865 is antipruritic in wild-type mice.

Example 4—Sedative Effects of PF-06372865 in Male C57BL/6 Mice

In order to exclude any sedative effects PF-06372865 might have on mice, a dose-response experiment is included. The mice receive per oral injections of PF-06372865 in varying doses (vehicle, 1, 3, 10, 30 and 100 mg/kg). After injection, the mice are placed in an open field arena and their activity is recorded for one hour starting one hour after injection. Mice show a significant increase in activity compared to mice that only received an injection of vehicle, excluding any sedative effects of PF-06372865 in wild-type mice.

Example 5—Effect of PF-06372865 on Non-Histamine-Induced Itch Model in Male C57BL/6 Mice A second pruritogen is included in order to confirm the antipruritic effect of PF-06372865 in wild-type animals, and to prove efficacy against non-histaminergic itch. The mice are dosed with PF-06372865 by oral gavage ninety (90) minutes before chloroquine injection. Doses of PF-06372865 are 1, 3, 10, 30 and 100 mg/kg. A dose-dependent reduction of scratching bouts by PF-06372865 treatment against chloroquine-induced itch is observed, confirming that PF-06372865 is antipruritic against non-histaminergic itch in wild-type mice.

Example 6—Effect of PF-06372865 on Contact Dermatitis Model in Male C57BL/6 Mice In order to assess the antipruritic effect of PF-06372865 in a clinically relevant disease, a contact dermatitis model of chronic itch is used. To this end, wild-type C57BL/6 mice are treated with 100 μL of 10% oxazolone (4-Ethoxymethylene-2-phenyl-2-oxazolin-5-one) dissolved in acetone/olive oil (4:1) on the nape of the neck. From day 7 to day 17 these mice are treated daily with 100 μL of 1% oxazolone dissolved in acetone/olive oil (4:1) on the nape of the neck to induce dermatitis and chronic itch. On day 18 the mice receive intraperitoneal injection of 10 mg/kg PF-06372865. The number of scratching bouts directed at the nape of the neck are recorded between 15 to 210 minutes after injection.

Example 7—Effect of PF-06372865 on Chronic Itch in Oxazolone-induced Itch Model in Male C57BL/6 Mice In order to assess: the antipruritic effect of PF-06372865 in a clinically relevant disease, the development of a tolerance towards the antipruritic effect of PF-06372865, and the effect of PF-06372865 in reducing dermatitis after prolonged treatment, the oxazolone-induced dermatitis model of chronic itch is used. To this end, wild-type C57Bl/6 mice are treated with 100 μL of 10% oxazolone (4-Ethoxymethylene-2-phenyl-2-oxazolin-5-one) dissolved in acetone/olive oil (4:1) on the nape of the neck. From day 7 to day 31 these mice are treated every other day with 100 μL 1% oxazolone to induce and maintain dermatitis and chronic itch. From day 17 onward, mice are treated with intraperitoneal injection of vehicle or 10 mg/kg PF-06372865 for thirteen consecutive days. On day 31, mice are given either intraperitoneal injection of vehicle or PF-06372865 (10 mg/kg). The number of scratching bouts directed to the nape of the neck between 15 to 210 min after injection are recorded. Mice that receive PF-06372865 injection on day 31 show a significant reduction in scratching bouts compared to mice receiving vehicle injection. This is independent of the treatment they received from day 7 to day 30. Mice receiving PF-06372865 treatment show the same reduction as mice receiving vehicle from day 7 to day 30 and PF-06372865 on day 31 as compared to mice receiving only vehicle or mice receiving PF-06372865 from day 7 to day 30 and vehicle on day 31. To quantify the severity of skin lesions, a dermatitis score are determined. Hemorrhage/erythema, dryness/scaring and hyperplasia (Yamada et. al. Exp Dermatol. 2016, 25, 611-617) are scored as 0 (none), 1 (mild), 2 (moderate) or 3 (severe) once per day resulting in a score between 0 and 9. Photographs of atopic dermatitis-like skin are taken before treatment (day 11) and 13 days after treatment (day 30). Mice that receive PF-06372865 show a significant reduction in skin lesions.

Example 8—Effect of PF-06372865 on Dry Itch Model in Male C57BL/6 Mice

In order to assess the antipruritic effect of PF-06372865 in another clinically relevant disease, the dry skin model of dermatitis is used. In the dry skin model, mice are treated with a mixture of acetone and diethylether (1:1) on the shaved nape of the neck for 15 s, followed by distilled water for 30 sec, twice daily for 10 days. On the day of the experiment, mice received intraperitoneal injection of vehicle or PF-06372865 (10 mg/kg). The number of scratching bouts directed to the nape of the neck between 15 to 210 min after injection are recorded. Mice that receive PF-06372865 injection show a significant reduction in scratching bouts compared to mice receiving vehicle injection.

Example 9—Effect of PF-06372865 on Bile Acid Itch Model in Male C57BL/6 Mice

In order to assess the antipruritic effect of PF-06372865 in another clinically relevant disease, the bile acid induced itch model is used. In the bile acid induced itch model, the fur at the base of the neck is shaved, and mice are placed in individual cylinders on a glass shelf. Mice are acclimatized to the experimental room, restraint apparatus and investigators for 2-hour periods on 2 successive days before experiments. The mice are dosed with 10 mg/kg PF-06372865 by oral gavage ninety (90) minutes before they are injected with deoxycholic acid. Deoxycholic acid (25 μg in DMSO), is administered by intradermal injection at the nape of the neck. Scratching behavior is quantified by 2 observers unaware of tested agents. A scratch is defined as lifting the hind limb to the injection site and then a placing of the paw on the floor, regardless of the number of strokes. If counts differed by greater than 5 scratches over a 30-minute period, both observers reevaluate the records. The number of scratching bouts directed to the nape of the neck between 15 to 210 min after injection are recorded. Mice that receive PF-06372865 injection show a significant reduction in scratching bouts compared to mice receiving vehicle injection.

Example 10—Effect of Repeat Dose of PF-06372865 on Oxazolone-Induced Dermatitis Study in Male C57BL6 Mouse Model The efficacy of the exemplary GABAA receptor modulator PF-06372865 as an antidermatitis agent is demonstrated using repeated doses of PF-06372865 in an Oxazolone-Induced Dermatitis Model in male C57BL/6 mice.

Male C57BL/6 Mice (8-10 weeks) are used in the study. Mice are housed one per cage and are maintained at controlled environmental conditions with 12-h light and dark cycles. The temperature and humidity of the room are maintained between 22±3° C. and 55±5%, respectively. The maximum and minimum temperature and relative humidity in the experimental rooms are recorded once daily.

NCT10004 Phosphate (Standard Compound) Formulation Preparation:

NCT10004 phosphate (adjusted with salt correction factor) is weighed into a clean glass container. 0.5% Methyl Cellulose (MC) is added, and the resulting mixture is mixed well using mild vortexing and stirred for 40 minutes to provide a homogeneous suspension.

NCT is weighed every day during treatment period and formulation prepared accordingly.

PF-06372865 (Test Compound) Formulation Preparation:

PF-06372865 is weighed into a clean mortar. 17% Liquefied Solutol is added drop wise and triturated using a pestle for 2-3 minutes, then 18% Glycerol formal is added and mixed in same fashion. The volume is made up by slowly adding the required volume of water. The resulting mixture is mixed well using mild vortexing to provide a homogeneous suspension. PF-06372865 is weighed every day during treatment period and formulation is prepared accordingly.

Oxazolone Preparation:

Oxazolone is weighed in a clean glass container and is dissolved in acetone/olive oil (4:1 v/v). The resulting mixture is mixed well using mild vortexing to form the desired strength solution.

| Oxazolone Strength | Oxazolone (mg) | Acetone/Olive oil (4:1 v/v) (mL) |
| --- | --- | --- |
| 10% | 600 | 6 |
| 1% | 30 | 3 |

Treatment groups:

| Group No. | Treatment Group |
| --- | --- |
| 1 | Vehicle, (10 ml/kg) 17% Solutol/ 18% glycerol formal/65% water (n = 16) |
| 2 | PF-06372865, 1 mg/kg, PO (n = 16) |
| 3 | NCT10004 Phosphate, 1 mg/kg, PO (0.5% Methyl Cellulose) (n = 8) |

Experimental Procedure

On Day '0' all mice are shaved with application of hair remover cream on neck area. On Day 1 Mice are sensitized by 100 μL topical application of 10% oxazolone dissolved in acetone/olive oil (4:1 v/v) on the nape of the neck.

After Day 1 Oxazolone application animals are kept in individual cages. Animals are not disturbed till Day 7 for any activity. From Day 7 to Day 31 these mice are topically applied every other day with 100 μL 1% oxazolone in acetone/olive oil (4: I v/v) to induce and maintain dermatitis and chronic itch.

Photographs of the skin are taken on Day 1, Day 17, and Day 30 prior to dosing. On Day 17 mice are randomized based on dermatitis scores and divided into three different groups as following:

| Group No. | Treatment | n | Dose | Dose Frequency | Route |
| --- | --- | --- | --- | --- | --- |
| 1 | Vehicle (17% Solutol 18% glycerol, 65% water) | 16 | 10 mL/kg | BID | PO |
| 2 | PF-06372865 | 16 | 1 mg/kg | BID | PO |
| 3 | NCT10004 | 8 | 1 mg/kg | BID | PO |

Animals are dosed with respective treatment groups for fourteen consecutive Days (From Day 17-Day 30). To quantify any changes in the severity of skin lesions, Animals are assigned dermatitis scores prior to dosing and daily there after starting from Day 17 and ending on Day 30.

Skin lesion are observed and scored as follows: Hemorrhage/erythema, dryness/scaling and hyperplasia are scored as 0 (none), 1 (mild), 2 (moderate) or 3 (severe) once per day resulting in a composite score between 0 and 9.

On Day 30, the two groups (Vehicle and PF-06372865) of mice are split again as following: Groups are dosed with vehicle or test article (PF-06372865) per oral (PO) such that the resulting four groups were:

1. Vehicle/Vehicle, (n=8)
2. Vehicle/PF-06372865, (n=8)
3. PF-06372865/Vehicle, (n=8)
4. PF-06372865/PF-06372865, (n=8)

NCT10004 treatment group are not divided.

On Day 30, animals are dosed with respective treatment groups and immediately after compound treatment, animals are kept in an empty transparent chamber (23 cm length×17 cm width) for acclimatization and observation.

Animals are observed by an observer blind to the treatment group for a period of 210 minutes post Oxazolone application. Number of scratching bouts directed to the nape between 15 to 210 min after dosing are recorded. For clarity sake, it should be noted that scratching bouts should be measured on the day after oxazolone application, and not the day of.

Severity of skin inflammation will increase in Vehicle treatment group compared to compound treatment from Day 22 onwards as will be evident by increase in lesion score in the Vehicle group. PF-06372865 treatment decreases skin lesions comparable to the NCT10004.

Increases in number of scratching bouts are observed across all treatment group when Oxazolone is applied topically. Observation the day after oxazolone application shows a significant change in number of scratching bouts in the treatment groups compared to Vehicle treatment when data was analyzed for 15-210 minutes duration.

Accordingly, these experiments demonstrate that administrative of PF-06372865 reduces scratching bouts in the Oxazolone dermatitis model.

Example 11—Effect of SL65.1498 on Histamine-Induced Itch

An additional GABAA positive allosteric modulator SL65.1498 is tested for its suitability as an antipruritic and/or anti-dermatitis agent by administering the compound in the Histamine-Induced Itch Model following a similar protocol as described in Example 1.

Example 12—Effect of AZD7325 on Histamine-Induced Itch

The GABAA positive allosteric modulator AZD7325 is tested for its suitability as an antipruritic and/or anti-dermatitis agent by administering the compound in the Histamine-Induced Itch Model following a similar protocol as described in Example 1.

Example 13—Effect of Diazepam on Histamine-Induced Itch

The GABAA positive allosteric modulator diazepam is tested for its suitability as an antipruritic and/or anti-dermatitis agent by administering the compound in the Histamine-Induced Itch Model following a similar protocol as described in Example 1.

Example 14—Effect of AZD6280 on Histamine-Induced Itch

The GABAA positive allosteric modulator AZD6280 is tested for its suitability as an antipruritic and/or anti-dermatitis agent by administering the compound in the Histamine-Induced Itch Model following a similar protocol as described in Example 1.

Example 15—Encapsulation of GABAA Positive Allosteric Modulators

A compound as described herein (2.5 g); corn starch (23 g); lactose (145 g), talc (15 g); and magnesium stearate (3.0 g); are mixed and encapsulated using techniques practiced in the art.

Example 16—Preparation of GABAA Positive Allosteric Modulators as Tablets

A compound as described herein (50 g); corn starch (50 g); lactose (125 g), magnesium stearate (2.0 g); and liquid petrolatum (2.0 g) are mixed using techniques practiced in the art. The resulting mixture is put through U.S. standard Screens to produce fine granules. The granules are compressed into tablets, each tablet containing about 75 mg of compound.

Example 17—Preparation of GABAA Positive Allosteric Modulators as a Syrup

Lemon oil (2 mL); Sucrose (650 g); citric acid (4 g); benzoic acid (3 g); and tragacanth (16 g) are dispersed in enough deionized water to make 800-900 mL of solution. A compound as described herein (25 g) is added and the resulting solution is stirred into a syrup. Additional deionized water is added to bring the total volume of syrup to 1000 mL.

Example 18—Packaging of GABAA Positive Allosteric Modulators

A compound as described herein (80 g) is added to propylene glycol (95 g) and milled until a finely divided uniform mixture is obtained. The mixture is then added to molten polyethylene glycol 4000 (1800 g). The resulting mixture is poured into molds, allowed to solidify and removed from the molds for packaging.

Example 19—Packaging of GABAA Positive Allosteric Modulators in Ampoules

A compound as described herein (30 g); hydroxypropyl beta-cyclodextrin (138 g); methylparaben (3 g); propylparaben (1 g); and lidocaine (5 g) are dissolved in enough deionized water to provide 1000 mL of solution. The solution is sterilized by filtration and filled into sterile ampoules using techniques practiced in the art.

Example 20—Preparation of GABAA Positive Allosteric Modulators as a Soft Gelatin Capsule A compound as described herein (1.5 g) is added to dimethylisosorbide (4.5 g). The mixture is warmed to about 60° C. with stirring until dissolved. To the resulting solution is added 7.5 g of LABRAFILRM® M 1944CS (apricot kernel oil PEG-6 ester) and 11.5 g of refined fish oil. The mixture is stirred until a homogeneous microemulsion concentrate forms. The microemulsion concentrate is introduced into a machine used to prepare soft capsules, which is adjusted so that 0.25 g of the microemulsion concentrate is injected into one soft capsule, to prepare the soft gelatin capsules.

While exemplary embodiments have been shown and described herein, it will be obvious to those skilled in the art that such embodiments are provided by way of example only. Numerous variations, changes, and substitutions will occur to those skilled in the art. It should be understood that various alternatives to the embodiments described herein may be employed. It is intended that the following claims define the scope of the disclosure and that methods and structures within the scope of these claims and their equivalents be covered thereby.

What is claimed is:

1. A method of treating or preventing itch in a mammal in need thereof, comprising administering to said mammal a pharmaceutical composition that comprises a therapeutically effective amount of a GABBA modulating compound of formula I, II, III or IV,

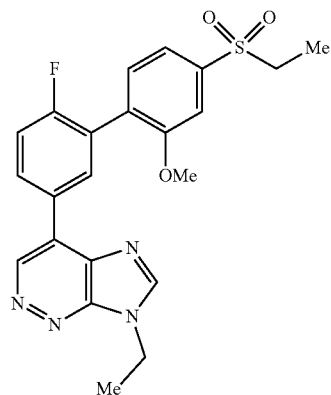

I

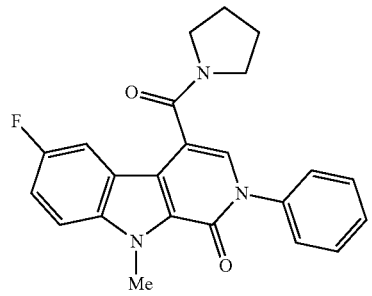

II

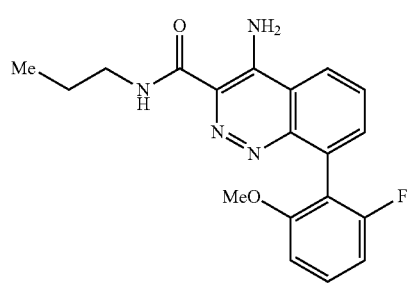

III or a pharmaceutically acceptable salt, solvate, hydrate, or co-crystal thereof.

2. The method of claim 1, wherein said pharmaceutical composition is administered orally.

3. The method of claim 1, wherein said pharmaceutical composition is administered through rectal administration.

4. The method of claim 1, wherein said pharmaceutical composition is administered parenterally.

5. The method of any one of claims 1-4, wherein the itch is associated with a disease or disorder selected from any of the following:
   (a) Skin conditions comprising any of dermatitis herpeformis, psoriasis, eczema, seborrheic dermatitis, atopic eczematous dermatitis, atopic dermatitis, summer recurrent dermatitis, contact dermatitis, irritant dermatitis, xerosis (dry skin), urticaria, hidradenitis suppurativa, lichen planus, lichen simplex, lichen simplex chronicus, lichen sclerosis, sweat gland abnormalities, bullous pemphigoid, pruritic urticarial papules and plaques of pregnancy (PUPPP), or gestational pemphigoid;
   (b) cholestasis resulting from any disorder comprising liver cirrhosis, gallstones, primary biliary cirrhosis, pregnancy, some medications or drugs, jaundice, hepatitis, abdominal masses, cystic fibrosis, or cancer;
   (c) renal disorders comprising chronic kidney disease, also known as uremic pruritus; hemodialysis, or cancer;
   (d) infections including fungal infections comprising vaginal or anal yeast infection, athlete's foot, or jock itch; viral infections comprising chicken pox, shingles, some sexually transmitted diseases; bacterial infections of the skin, including acne; and parasitic infections or infestations comprising scabies, lice or worm infections; or swimmer's itch;
   (e) insect bites or stings comprising those from mosquitoes, fleas, chiggers, spiders, scorpions, biting flies, bees, wasps, hornets, mites, or ants;
   (f) medications or other chemicals including allergy to psychiatric medications or antibiotics in particular; morphine and other opioid-induced itch; photodermatitis, where sunlight reacts with chemicals in the skin forming irritant molecules; or chemotherapy;
   (g) other causes comprising cancers of the blood such as Hodgkin's disease; skin cancers; cutaneous T-cell lymphoma; other forms of cancer; polycythemia, which can cause generalized itching due to increased histamine; thyroid illnesses; shaving; diabetes mellitus; dandruff, iron deficiency such as anemia; psychogenic itch; stress and stress disorders; sunburn; senile itch; idiopathic itch; burns; wound healing; skin blisters; prurigo nodularis; chronic pruritus; and neurogenic itch, or itch related to nerve damage; multiple sclerosis; or pinched nerves.

6. The method of any one of claims 1-4, wherein the itch is associated with atopic dermatitis, uremic pruritus, or neuropathic itch.

7. A method of treating or preventing dermatitis in a mammal in need thereof, comprising administering to said mammal a pharmaceutical composition that comprises a therapeutically effective amount of a GABBA modulating compound selected from PF-06372865, SL65.1498, AZD7325, and AZD6280, or a pharmaceutically acceptable salt, solvate, hydrate, or co-crystal thereof.

8. The method of claim 7, wherein said pharmaceutical composition is administered orally.

9. The method of claim 7, wherein said pharmaceutical composition is administered through rectal administration.

10. The method of claim 7, wherein said pharmaceutical composition is administered parenterally.

11. The method of any one of claims 7-10, wherein said dermatitis is selected from eczema, atopic dermatitis, seborrheic dermatitis, contact dermatitis, irritant dermatitis, summer recurrent dermatitis, and dermatitis herpetiformis.

12. The method of any one of claims 1-11, wherein said compound is PF-06372865.

13. The method of any one of claims 1-11, wherein said compound has a structure of Formula I, 14. The method of any one of claims 1-11, wherein said compound is SL65.1498.

15. The method of any one of claims 1-11, wherein said compound has a structure of Formula II, 16. The method of any one of claims 1-11, wherein said compound is AZD7325.

17. The method of any one of claims 1-11, wherein said compound has a structure of Formula III,

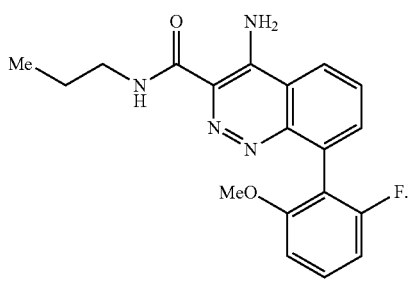

Formula III

18. The method of any one of claims 1-11, wherein said compound is AZD6280.

19. The method of any one of claims 1-11, wherein said compound has a structure of Formula IV, Formula IV

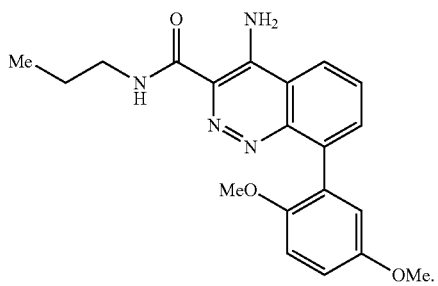

20. The method of any one of claims 1-19, wherein said pharmaceutical composition comprises an emulsifying agent, a percutaneous penetration enhancer, a suspending agent, water, or any combination thereof.

21. The method of claim 20, wherein said emulsifying agent comprises an ethoxylated fatty acid.

22. The method of claim 20, wherein said percutaneous penetration enhancer comprises glycerol.

23. The method of claim 20, wherein said suspending agent comprises hydroxypropyl-beta-cyclodextrin.

24. The method of any one of claims 1-23, wherein the therapeutically effective amount comprises from about 0.01 mg to about 200 mg of the GABAA modulating compound.

25. The method of claim 24, wherein the wherein the therapeutically effective amount comprises from about 0.05 mg to about 100 mg of the GABAA modulating compound.

26. A medicament for use in the treatment or prevention of itch or dermatitis, said medicament comprises a therapeutically effective amount of a compound of Formula I, II, III, or IV:

I

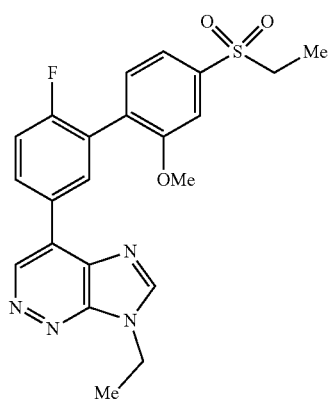

II

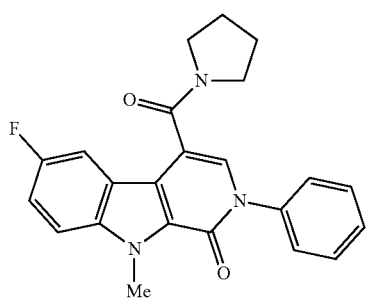

III

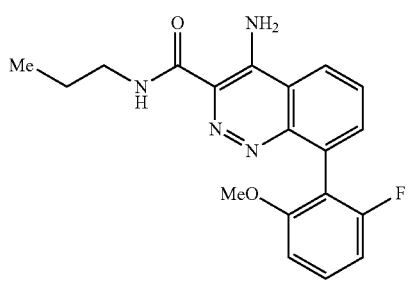

IV

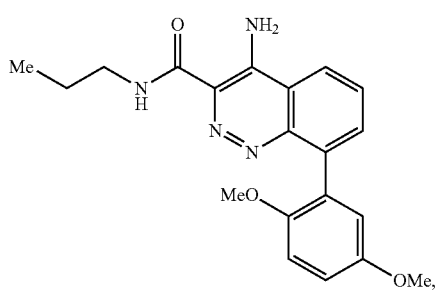

or pharmaceutically acceptable, salt, solvate, hydrate, or co-crystal thereof.

* * * * *